United States Patent
Cumberland et al.

(10) Patent No.: US 7,407,624 B2
(45) Date of Patent: Aug. 5, 2008

(54) METHOD FOR ABATEMENT OF ALLERGENS, PATHOGENS AND VOLATILE ORGANIC COMPOUNDS

(75) Inventors: John Ross Cumberland, Corona Del Mar, CA (US); James L. Driver, Irvine, CA (US)

(73) Assignee: Prompt Care, Inc., Costa Mesa, CA (US)

(*) Notice: Subject to any disclaimer, the term of this patent is extended or adjusted under 35 U.S.C. 154(b) by 70 days.

(21) Appl. No.: 11/275,192

(22) Filed: Dec. 16, 2005

(65) Prior Publication Data

US 2006/0140817 A1 Jun. 29, 2006

Related U.S. Application Data

(63) Continuation-in-part of application No. 10/959,822, filed on Oct. 6, 2004, which is a continuation of application No. PCT/US03/11800, filed on Apr. 14, 2003.

(60) Provisional application No. 60/373,738, filed on Apr. 16, 2002.

(51) Int. Cl.
*A61L 9/00* (2006.01)
*A62B 7/08* (2006.01)
*B01J 19/08* (2006.01)

(52) U.S. Cl. .................. 422/28; 422/29; 422/34; 422/121; 422/123; 422/124; 422/186; 422/186.07; 422/305

(58) Field of Classification Search ............ 422/28–29, 422/34, 121–124, 186, 186.07, 305
See application file for complete search history.

(56) References Cited

U.S. PATENT DOCUMENTS

| | | | | |
|---|---|---|---|---|
| 4,086,152 A | * | 4/1978 | Rich et al. ................. | 204/176 |
| 4,309,388 A | * | 1/1982 | Tenney et al. ............. | 422/304 |
| 4,842,829 A | * | 6/1989 | Hirai et al. ............. | 422/186.08 |
| 5,259,962 A | * | 11/1993 | Later ...................... | 210/758 |
| 5,578,280 A | | 11/1996 | Kazi et al. | |
| 5,656,246 A | * | 8/1997 | Patapoff et al. ............ | 422/187 |

(Continued)

FOREIGN PATENT DOCUMENTS

EP 0 431 648 12/1991

(Continued)

OTHER PUBLICATIONS

Internet Printout for "Appendix B, Useful Conversion Tables" from website: www.lifewater.ca/Appendix_B.htm, Apr. 28, 2007.

(Continued)

*Primary Examiner*—Jill Warden
*Assistant Examiner*—Monzer R Chorbaji
(74) *Attorney, Agent, or Firm*—Knobbe, Martens, Olson & Bear LLP

(57) ABSTRACT

The present invention pertains to methods utilizing ozone treatment for abating allergens, pathogens, odors, and volatile organic compounds. The methods can be employed to abate pollutants, bacteria, viruses, mold, dander, funguses, dust mites, animal and smoke odors, and the like. The methods employ specific combinations of ozone concentration, hydrogen peroxide concentration, temperature, and humidity delivered over a specified period of time to achieve satisfactory abatement of the allergen, pathogen, odor, or volatile organic compound.

40 Claims, 4 Drawing Sheets

U.S. PATENT DOCUMENTS

| | | | | |
|---|---|---|---|---|
| 5,752,878 | A | | 5/1998 | Balkany |
| 5,868,999 | A | | 2/1999 | Karlson |
| 6,096,266 | A | * | 8/2000 | Duroselle ................ 422/33 |
| 6,279,589 | B1 | * | 8/2001 | Goodley ................ 134/102.1 |
| 6,313,470 | B1 | | 11/2001 | Fencl et al. |
| 6,327,812 | B1 | | 12/2001 | Hedman et al. |
| 6,365,103 | B1 | | 4/2002 | Fournier |
| 6,487,868 | B2 | | 12/2002 | Sato et al. |

FOREIGN PATENT DOCUMENTS

EP            0 431 648 A1 * 12/1991

OTHER PUBLICATIONS

Rice, Rip G. *Ozone and Anthrax—Knowns and Unknowns*, Ozone Science & Engineering vol. 24 pp. 151-158, Apr. 16, 2002.

Yokozeki, et al. *Disinfection of Poultry Breeding Environment Using Ozone gas. Application to the Disinfection of Workers Shoes*, Chikusan No Kenkyu 49 (9) 1009-1012 (1995) (Abstract not available).

Naitoh, S et al. *Studies on the Application of Ozone in Food Preservation: Effect of Ozone Treatment on Aerial Contaminants in a Plastics Film Factory*, J. Antibacterial and Antifungal Agents, Japan 21 (8): 445-451 (1993) (Abstract Only).

Chun, et al. *Sterilizing and Deodorizing Effect of UV-Ray Air Cleaner for Refrigerator*, Korean J. Food Sci. Technol. 25 (2): 174-177. (1993) (Abstract Only).

Kuprianoff, J, *The Use of Ozone for the Cold Storage of Fruit*, Z. Kaitentechnik 10:1-4 (1953) (Abstract Only).

Naitoh, S. *Studies on the Utilization of Ozone in Food Preservation—Effect of Ozone Treatment on Airborne Microorganisms in a Confectionery*, J. Antibact. Antifung. Agents 17 (10) 483-489 (1989) (Abstract Only).

Whistler, et al. *Biocidal Activity of Ozone Versus Formaldehyde Against Poultry Pathogens Inoculated in a Prototype Setter*, Poultry Science 68 1068-1073 (1989) (Abstract Only).

Yokozeki, et al. *Disinfection of Poultry-Farm Environment—Repellent Effect of Ozone gas against rat and mouse*, Chikusan no Kenkyu 49 (10): 1114-1118 (1995). (Abstract not available).

Lechevallier M. *Ozone v. Viruses* Manuscript by Sobsey & LeChevallier University of North Carolina (Abstract only), date unknown.

Beglund et al. *Ozone Related Case Studies with Independent Consultant Summaries*, CFR Environmental Cleaning Systems, date unknown.

Kells, et al, *Efficacy and Fumigation Characteristics of Ozone in Stored Maize*, Journal of Stored Products Research 37, 371-382 (2001).

International Search Report for equivalent PCT International Application No. PCT/US03/11800, Aug. 21, 2003.

PCT International Application No. PCT/US03/11800 filed Apr. 14, 2003.

Russian Department of Health, *Importance of Ozone*, Journal Priroda (1976) (Abstract Only).

* cited by examiner

METHOD FOR ABATEMENT OF ALLERGENS, PATHOGENS AND VOLATILE ORGANIC COMPOUNDS

CROSS-REFERENCE TO RELATED APPLICATIONS

This application is a continuation-in-part of application Ser. No. 10/959,822, filed Oct. 6, 2004, which is a continuation, under 35 U.S.C. § 120, of International Patent Application No. PCT/US03/11800, filed Apr. 14, 2003 under the Patent Cooperation Treaty (PCT), which was published by the International Bureau in English on Oct. 30, 2003, which designates the United States, and which claims the benefit of U.S. Provisional Patent Application No. 60/373,738, filed Apr. 16, 2002, the disclosures of which are hereby incorporated by reference in their entirety and are hereby made a part of this specification.

FIELD OF THE INVENTION

The present invention pertains to methods utilizing ozone treatment for abating allergens, pathogens, odors, and volatile organic compounds. The methods can be employed to abate pollutants, bacteria, viruses, mold, dander, funguses, dust mite allergens, animal and smoke odors, and the like. The methods employ specific combinations of ozone and hydrogen peroxide concentration, temperature and humidity delivered over a specified period of time to achieve satisfactory abatement of the allergen, pathogen, odor, or volatile organic compound.

BACKGROUND OF THE INVENTION

Building-Related Illness (BRI) is a discrete, identifiable disease or illness that can be traced to a specific pollutant or source within a building. In contrast, the term Sick Building Syndrome (SBS) is used to describe situations in which building occupants experience acute health and comfort effects that appear to be linked to time spent in a building, but no specific illness or cause can be identified. Both syndromes are associated with immediate or potential health problems and are of particular concern as it is estimated that most people spend as much as 90% of their time indoors. It is indoors where EPA studies have shown that the levels of pollutants can be 2-5 times, and occasionally, more than 100 times higher than outdoor levels.

The American Lung Association recently documented a decrease in motivation, performance, and productivity among office workers and school children in relation to poor indoor air quality within buildings. Their evidence involving office workers suggests that when individuals experience only two symptoms of discomfort, they begin to perceive a reduction in their own performance. This perception increases as the number of symptoms increases, averaging 3% loss with three symptoms, and an 8% loss with five symptoms.

The EPA stated in 1991, "The term "Sick Building Syndrome" is used to describe situations in which building occupants experience acute health and discomfort effects that appear to be linked to time spent in a building, but no specific illness or cause can be identified. The complaints can be localized in a particular room or zone, or can be widespread throughout the building. In contrast, the term "Building Related Illness" is used when symptoms can be attributed directly to airborne building contaminants." The EPA has just published a new reference document, "Mold Remediation in Schools and Commercial Buildings" (EPA 402-K-01-001). This publication is the governmental standard for mold and treatment of commercial buildings. The EPA states that mold in commercial buildings contaminates or destroys everything it grows on including building walls, air conditioning, ceiling and carpeting, etc.

Identifying "Sick Buildings" can be difficult. Identifying the actual cause of the 'sickness' can be even more difficult. Molds are a good example of the problems encountered when attempting to identify the source of pollutants. They are present everywhere, both indoors and outdoors. Their effects on people are quite random, some experience extreme symptoms, while others have only minor reactions.

Those who suffer from asthma, hay fever, or other allergies are at a particularly high risk for Building-Related Illnesses. Symptoms can include one or more of the following (ranging from mild to acute): headache; eye, nose or throat irritation; dry or itchy skin; dizziness and nausea; difficulty in concentrating; fatigue; and sensitivity to odors. In the case of Building Related Illnesses, the cause of the symptoms is not obvious, i.e., a cold or flu. The symptoms can linger for several weeks or more. Most of the affected people experience relief after leaving the building. If inhabitants of a building experience these symptoms, then the building's environment can be a factor.

Unhealthy indoor air associated with Sick Building Syndrome and Building Related Illnesses can come from a variety of sources. Most common are dust mites (and their feces), mold, off-gassing chemicals (from carpets, paint, glues and plastics), and natural sources (decaying plants or animals, radon, animals and their dander, people). Many substances can infiltrate our indoor airspaces and then accumulate to a point that leads to illness.

Molds (fungi) can often be associated with Sick Building Syndrome and Building-Related Illnesses. According to an Environmental Protection Agency (EPA) bulletin published in March 2001, "Molds can be found almost anywhere; they can grow on virtually any organic substance, as long as moisture and oxygen are present. There are molds that can grow on wood, paper, carpet, foods, and insulation. When excessive moisture accumulates in buildings or on building materials, mold growth will often occur, particularly if the moisture problem remains undiscovered or unaddressed."

Indoors and outdoors, mold is present everywhere. The term mold applies to the microscopic members of the Fungi kingdom. It is a fuzzy, cobweb-like growth produced on organic matter. Mold has no ability to 'fix' carbon using chlorophyll, so it relies on some type of organic material as a food source. It can spread rapidly, forming the mycelium (fungal body), which is made up of a fine network of filaments (hyphae). The mycelium produces other clusters of root like hyphae, called rhizoids, which penetrate the organic material, secreting enzymes and absorbing water and the digested sugars and starches. Other clusters of hyphae called sporangiophores then reach upward, forming sporangia (knoblike spore cases), which bear the particular color of the mold species. Upon ripening, the sporangia break open and the windborne spores land elsewhere to reproduce asexually. If they find themselves in a less than ideal situation (not sufficient food, water, etc) molds are likely to switch to a nonsexual method of reproduction (one not involving swapping or combining of genetic material) for the duration. This can make molds hard to identify, since species are classified by their sexual characteristics (e.g., kind of spore cell wall, spore-producing cells, and sacs that store cells). Worldwide there are more than 100,000 species of mold, with at least 1,000 species common in the United States. Some of the most commonly found are species of *Cladosporium, Penicillium,* and *Aspergillus*. Mold can be found almost everywhere and it can grow on virtually any organic substance. Mold is most likely to grow where there is water or dampness, such as bathrooms, attics, and basements.

Most types of mold commonly encountered are not hazardous to healthy individuals. However, there are some that have achieved recent notoriety that are strongly toxic such as *Stachybotrys*. *Stachybotrys* is not common but can be very harmful when encountered in quantity. Others, like *Aspergillus*, can be dangerous as well. Aspergillosis is a lung disease suffered generally by immune-compromised people. In this disease, the *Aspergillus* mold actually grows in a person's lungs and can cause death. In general, too much exposure to even common molds can cause or worsen conditions such as asthma, hay fever, or other allergies. Common symptoms of overexposure to mold are cough, congestion, runny nose, eye irritation, and aggravation of asthma. More serious health effects, such as fevers and breathing problems, can occur depending on the amount of exposure and person's individual vulnerability.

When moldy material becomes damaged or disturbed, spores (reproductive bodies similar to seeds) can be released into the air. Exposure can occur if people inhale the spores, directly handle moldy materials, or accidentally ingest it. Mold can sometimes produce chemicals called Mycotoxins, which can also cause illness to sensitive people.

All molds must have water to grow. Mold can grow almost anywhere there is water damage, high humidity, or dampness. Removing the source of moisture is critical to preventing mold growth. Typical water sources utilized by mold in residential environments include air conditioner condensers, roof leaks, pipe leaks, sprinklers adjacent to an outside wall, and the like.

*Stachybotrys Chartarum* (also known as *Stachybotrys atra*) is a type of mold that has been associated with health effects in people. It is a greenish-black mold that can grow on materials with a high cellulose content, such as drywall, hanging ceilings and wood—that has been chronically moist or water damaged, due to excessive humidity, water leaks, condensation, or flooding. Numerous molds are black in appearance, but are not *Stachybotrys*. For example, the black mold commonly found between bathroom tiles is not *Stachybotrys*. *Stachybotrys* can only be positively identified via laboratory testing.

Indoor levels of *Stachybotrys* are typically low; however, as with other types of mold, at higher concentrations health effects can occur. These include allergic rhinitis (cold-like symptoms), dermatitis (rashes), sinusitis, conjunctivitis, and aggravation of asthma. Some related symptoms are general, such as inability to concentrate and fatigue. Usually, symptoms disappear after the contamination is removed.

There has been some evidence linking *Stachybotrys* with pulmonary hemosiderosis in infants who are generally less than six months old. Pulmonary hemosiderosis is an uncommon condition that results from bleeding in the lungs. In studies of pulmonary hemosiderosis, the exposure to *Stachybotrys* came from highly contaminated homes, where infants were continually exposed over a long period of time. Individuals exposed to the mold who exhibit symptoms characteristic of mold exposure should seek appropriate medical attention.

Visible mold can be sampled and analyzed by laboratories specializing in microbiology. However, these tests can be expensive—from hundreds to thousands of dollars. Even if a building is tested for mold, it is difficult to determine at what levels health effects can possibly occur. Therefore, it is important to attack any mold infestation. For small infestations, bleach and water can be effective to kill the mold growth. For larger infestations, more extensive treatment wherein large areas of a building or the whole building are treated can be necessary to kill all of the mold. Once the mold is destroyed, the next step is to find the mold's source of water. Mold will not grow without water, so to prevent its return, its source of water must be located and eliminated. In order to adequately remediate a mold infestation, it is necessary to both destroy the mold and to eliminate the mold's source of water.

While mold infestation itself is not becoming more common, knowledge of it and the problems it can cause is becoming more widely disseminated. In the last few years there have been many widely publicized cases concerning sicknesses caused by mold and the multi-million dollar settlements awarded to those who suffered the consequences of mold toxicity. As well, there have been reports of individuals who have burned their houses down because that was a cheaper solution than remediation of the mold-caused damage. Removal of moldy materials can involve procedures similar to those associated with removal of toxic waste material, such as asbestos, which means that any remediation can be extremely expensive to conduct. It is because of all this publicity that there is an appearance that mold has become more prevalent when in fact it has only become more recognized for its undesirable qualities.

Other pathogens, allergens, and odor-causing agents, e.g., dust mite feces, fungi, spores, pollen, mildew, bacteria, viruses, amoebas, fragments of plant materials, human and animal dander, proteins that that cause allergic reaction such as the ones in dust mite feces and animal dander, feather dust, litter dust, tobacco smoke, smoke from fires, volatile organic compounds, and other bio-aerosols and inorganic aerosols and gases, can also be the cause of Building Related Illnesses. For example, the feces of household dust mites can cause allergic reactions. A gram of house dust (approximately half of a teaspoon) can contain as many as 1,000 dust mites. That same amount of dust could hold over 250,000 of their fecal pellets. Once airborne, dried dust mite droppings are so small that they are easily inhaled causing allergic reactions in many people. These reactions can range from sneezing, coughing, itchy eyes and sniffles to asthma, eczema, even snoring. House dust mites are related to spiders. They are eight legged creatures invisible to the human eye. They survive by eating dead skin cells. A dust mite will produce 20 fecal pellets per day, which is 200 times its own body weight, during its short lifetime. The greatest number of dust mites in the home is usually found in the bedroom, specifically in the bedding and pillow. The skin and moisture shed each night provide ideal conditions for their growth. Millions of mites can be present in bedding, and up to 10% of a two-year-old pillow's weight can be made up of house dust mites and their droppings.

Pets are another source of allergens. Household pets are the most common source of allergic reactions to children. It is estimated that 10 million animal owners may be allergic to their animals, and 20% to 30% of the people who have asthma are also allergic to animals. Many people react to animal allergies in extremely different manners. For some people, animal odors, dander, saliva, and urine can cause allergic reactions. Animal fur can also collect outdoor pollens, mold spores, and other outdoor allergens that are then brought indoors. A recent study reviewed by the American Academy of Allergy, Asthma and Immunology, indicated that approximately 80% of the animal owners surveyed keep their animals indoors most of the time. These findings may help explain why allergy symptoms, such as itchy and watery eyes, sneezing, coughing, wheezing and hives in allergic children and adults, worsen with continued exposure to animals.

The American Lung Association's "Health House Project" stated that "[a]ccording to a recent study published in Pediatrics magazine, asthma cases could drop nearly 40% among America children under age 6 if susceptible youngsters did not have pets or other allergy triggers in their home. The study also found that children with animal allergies were 24 times more likely to have asthma than those without such allergies."

One of the more difficult problems with allergies to animals is it can take two years or more to develop in a home and may not subside until 6 months or more after the animal has been removed from the home. Carpeting and furniture can act as reservoirs for animal dander and allergens. The animal dander can become a food source for common household dust mites. These pest and allergens can also find their way throughout the homes' heating and air condition system.

The elderly, young children and infants in particular, are especially susceptible to negative reactions to allergens and pathogens. Many magazines, such as Harper's Bazaar and Parent's have articles on how to clean and prepare a home for a new infant. Harper's has a Wellness Report that contains a home purity checklist that cites mold, dust mites, and animal dander as major home health concerns. As mentioned above, of major concern to infants is animal dander that can trigger sniffling, stuffy noses, and sneezing and water eyes. Dust mites are a known trigger for asthma, and found everywhere.

Of serious concern to infants is mold, which comes from persistent leaks from air conditioners and plumbing that can lead to airborne mold, which aggravates allergies. Some indoor molds have the potential to produce extremely potent toxins called Mycotoxins. Mycotoxins are readily absorbed by the intestinal lining, airways, and skin. Molds that produce potent toxins have been associated with acute pulmonary hemorrhage among 37 infants from the Cleveland, Ohio, area between 1993 and 1998. Twelve of these children died. As stated by Dr. Henry Fishman M. D. P. C., Diplomat American Board of Allergy and Immunology, American Board of Internal Medicine and National Board of Medical Examiners, "There is a body of evidence that indoor allergies, particularly dust mites, may cause asthma in some infants. Without the dust mite sensitivity, asthma does not develop. Untreated asthma in pregnant women can lead to early deliveries, miscarriages, and low birth weight infants. Indoor allergens can make this worse. Also allergies can lead to infections. Kids' immune systems cannot handle the infections burden as well as an adult. So kids with allergies have trouble with infections which can bother their tiny lungs. In other words, in some sensitive kids, allergies have a huge impact on their nose, sinuses and lungs."

Commercial buildings often present special concerns regarding Sick Building Syndrome, Building Related Illnesses. According to Business Week Magazine, today's business office is home to as many as 30 different volatile organic chemicals released by building materials, furnishing and office equipment. Some of the biggest offenders are sealed windows, carpets and padding, carcinogenic cleaning products, the office restroom, cafeterias and kitchen areas, and building renovations. Many people work in enclosed building or offices. Not being able to open windows means you do not always have enough fresh air to circulate within the building. Many carpets, rugs, and paddings are made in part from petrochemicals. An example is formaldehyde odor which is often noticed for a few weeks after new carpet is installed. The same is true with products used in the interiors of new cars. The odor being released is called "out gassing." It often affects people with allergies or sensitive skin. There are over 70,000 identified chemical cleaning products on the market that are used to clean buildings and offices. Some of them contain toxic solvents that, it is claimed, are considered safe when used properly. Clogged toilets and flooded restrooms can create toxic mold and airborne mold spores in area that are difficult to continually inspect. Many buildings have common lunch and food areas that must be maintained within local Health Department standards. Office construction and remodeling can cause mold to spread throughout a building in the matter of a few minutes according to EPA testing. Mold and contaminated dust can cause employees serious health problems.

Problems associated with Sick Building Syndrome have been extensively reported in the media. Media coverage has shown buildings being condemned; structures being burned down to destroy toxic and mold contaminates. Business and consumer magazines such as *Business Week, Time, The Wall Street Journal, Reader's Digest* and *People Magazine* are reporting insurance claims cases and medical awards to people that have been harmed by these toxic conditions. In every case, the courts decisions held that the condition could and should have been treat earlier by the building owners or insurance companies. Television networks are giving coverage to this problem as a major health and business issue.

Erin Brockovich, antipollution crusader, was featured on CBS News broadcast "48 Hours," because her home is infested with the toxic *stachybotrys* mold. NBC Nightly News coverage of the Melinda Ballard's toxic infestation case stated "A Texas jury decided her insurer committed fraud and mishandled her claim, awarding her $32 million."

In the August, 2000 issue of *Claims Magazine*, an insurance industry publication, "a jury recently awarded more than $40 million in personal injury claims. There were over 200 workers' compensation claims and at least 180 separate lawsuits. Previously, such lofty figures were seen only in asbestos or drug-related class actions. Now, we are starting to hear 11-digit figures mentioned in litigation concerning the lowly mold fungi."

*The Lawyers Weekly USA*, a national publication, stated in their Oct. 6, 2000 edition, that claims for personal injury and property damage caused by mold growing inside buildings are on the rise, and one of the "hottest areas" in construction defect and toxic tort law.

The United Press International reports in a feature story titled "Toxic mold a growing legal issue" that, "Mold contamination claims were virtually unheard of a few years ago, but people are becoming more aware of indoor air quality issues because of the expanding scientific and medical knowledge of the toxic effects of mold.

SUMMARY OF THE INVENTION

A method for abating or remediating pathogens or allergens in a commercial or residential setting that ensures the elimination of the maximum number of chemical pollutants, bacteria, viruses, mold, allergens and other fungi, as well as urine and smoke odors possible within the treated area is therefore desirable. It is also desirable that the method leaves no residual chemicals behind, only a fresh, clean smell. A method that may be conducted by trained technicians in a safe and time effective manner, and may preferably be completed at a time when the premises is likely to be vacated (working/school hours for a home, evening hours for an office/commercial location), allowing minimal disruption to a company's or family's daily routine is desirable as well. Particularly desirable is a method that is capable of treating both small as well as large interior areas, and multi-floor or separate locations, as well as major infestations of various types of molds, including toxic molds, without the need for hazardous material precautions, is also desirable. The process of abating can include, but is not limited to, killing, destroying, neutralizing, lessening the strength or effectiveness of, converting, or otherwise reducing the harmful or undesirable effects of the pathogen, allergen, volatile organic compound, or other substance.

It is noted that tabletop and room unit ozone generators are marketed to the consumer as means of improving indoor air quality. *Consumer Reports* (1992), the National Institute of Occupational Safety and Health (NIOSH) (Boeniger, 1995), and the U.S. EPA (1995) concluded that tabletop and room unit ozone generators are not effective in improving indoor air quality. A recent study by the U.S. EPA concluded that ozone is not effective for killing airborne molds and fungi even at high concentrations (6-9 ppm) (U.S. EPA, 1995). In contrast to this earlier work, it has been determined that selected conditions of ozone concentration, hydrogen peroxide, humidity, and temperature are highly effective at killing airborne molds and fungi at even lower ozone concentrations.

Although mold abatement is primarily referred to in regard to the preferred embodiments, it is to be understood that the methods described are suitable for use in abating other substances, including, but not limited to, pathogens, allergens, and odors, including, but not limited to, dust mite allergens, other fungi, spores, pollen, mildew, bacteria, viruses, amoebas, fragments of plant materials, human and animal dander, feather dust, litter dust, tobacco smoke, volatile organic compounds, and other bioaerosols and inorganic aerosols and gases.

In preferred embodiments, ozone (commonly referred to as activated oxygen) in combination with hydrogen peroxide is used in the abatement process. Ozone is one of the most powerful sanitizers and deodorizers known. Ozone is a natural component of ambient air. The highest levels of naturally occurring ozone are found in forests, mountains and along seashores. Ozone is created when the energy from ultra violet light or an electrical discharge changes the oxygen molecules ($O_2$) into ozone ($O_3$). This ozone molecule is highly unstable and readily reverts back to $O_2$. When it does revert back to $O_2$ the extra oxygen atom that it releases may react with another compound (for example a malodorous compound, or the surface of an allergen, germ, or mold) changing that compound or microorganism in the process.

Alternatively the extra atom of oxygen may react with a molecule of water ($H_2O$) to produce a 'hydroxyl radical' (—OH). Hydroxyl radicals have been demonstrated to be highly destructive to other molecules containing carbon or sulfur bonds (single or double). In fact the hydroxyl molecule is significantly more reactive than ozone. In air, the number of hydroxyls produced by the decomposition of ozone is highly dependent on the amount of water vapor present (humidity). In general, the higher the humidity, the larger the number of hydroxyls produced and the more reactive the air, ozone, hydroxyl mixture becomes.

The number of hydroxyls produced by ozone can be significantly increased if the air contains the chemical hydrogen peroxide ($H_2O_2$). Hydrogen peroxide rapidly decomposes into hydroxyl radicals when attacked by ozone. In the preferred embodiment, hydrogen peroxide is added to an ultrasonic humidifier used to provide and control humidity in the treated areas. Given sufficient ozone, and an abundance of airborne hydrogen peroxide over a short period of time, enough oxygen atoms and hydroxyl radicals are produced to effectively convert the polluting or otherwise undesirable substances present into new and typically less contaminating or harmful ones.

Bacteria, fungi (molds and mildew) which can cause unpleasant odors, allergic reactions and sometimes disease, are destroyed when they come into contact with ozone and/or the hydroxyl radical. As with chemical pollutants, the outer membranes or shells of these microorganisms contain receptors that ozone/hydroxyl attacks and, if sufficient ozone/hydroxyl is present, break down. Without its protective membrane or shell, the microorganism dies quickly.

The methods of preferred embodiments utilize the chemical characteristics of ozone and hydrogen peroxide to generate a highly effective natural sanitizer while ensuring the proper protection for building occupants and technicians administering the treatment. The end result is a highly purified space with cleaned air containing oxygen as a residual substance generated by the process.

In a first aspect, a method for abating a substance is provided, the method comprising the step of: exposing a substance selected from the group consisting of a pathogen, an allergen, and an odor-causing agent to a gaseous atmosphere comprising water vapor, ozone, and hydrogen peroxide, wherein the atmosphere has an ozone concentration of from about 2 to about 10 parts per million, a relative humidity of from about 50% to about 90%, a hydrogen peroxide concentration that is from about 75% to about 150% by weight of the ozone concentration, and a temperature of from about 15° C. to about 27° C., wherein the substance is exposed to the atmosphere for a time period of from about 0.5 hours to about 3 hours, whereby the substance is abated.

In an embodiment of the first aspect, the pathogen is selected from the group consisting of mold, Norwalk virus, and anthrax.

In an embodiment of the first aspect, the allergen is selected from the group consisting of dust mite feces, dander, tobacco smoke, and a protein capable of inducing an allergic reaction in a human susceptible thereto.

In an embodiment of the first aspect, the odor-causing agent is selected from the group consisting of a volatile organic compound and urine.

In a second aspect, a method for abating a substance in an space is provided, the method comprising the steps of: sealing a space such that conditions of ozone concentration, temperature, hydrogen peroxide concentration, and relative humidity within the space can be controlled, wherein the space contains at least one substance selected from the group consisting of a pathogen, an allergen, and odor-causing agent; maintaining an atmospheric ozone concentration in the space of at least about 2 ppm; maintaining an atmospheric hydrogen peroxide concentration in the space, wherein the atmospheric hydrogen peroxide concentration is at least about 75% by weight of that of the atmospheric ozone concentration; maintaining a relative humidity within the space of at least about 50%; and maintaining a temperature within the space of at least about 15° C.; wherein the steps are conducted substantially simultaneously for a time period of at least about 0.5 hours, whereby the substance is abated.

In an embodiment of the second aspect, the atmospheric ozone concentration is from about 2 to about 10 parts per million, the relative humidity is from about 50% to about 90%, the atmospheric hydrogen peroxide concentration is from about 75% to about 150% by weight of the atmospheric ozone concentration, the temperature is from about 15° C. to about 27° C., and the time period is from about 0.5 hours to about 3 hours.

In an embodiment of the second aspect, the method further comprises the step of ceasing providing ozone to the space; and thereafter exposing an interior of the space to ultraviolet light, whereby an odor associated with ozone is reduced.

In an embodiment of the second aspect, the method further comprises the step of ceasing providing ozone to the space; and thereafter exposing the space to a temperature above 27° C., whereby an odor associated with ozone is reduced.

In an embodiment of the second aspect, the method further comprises the step of providing ions to the space, whereby an odor associated with ozone is reduced.

In an embodiment of the second aspect, the space comprises an interior portion of a building.

In an embodiment of the second aspect, the space comprises a room of a building.

In an embodiment of the second aspect, the building comprises a dwelling.

In an embodiment of the second aspect, the space comprises an interior portion of a ship.

In an embodiment of the second aspect, the space comprises an interior portion of passenger car.

In an embodiment of the second aspect, the space comprises an interior portion a mobile home or a motor home.

In a third aspect, a method for abating a substance in an enclosed space is provided, the method comprising the steps of: providing an ingress into the space, wherein the space contains at least one substance selected from the group consisting of a pathogen, an allergen, and odor-causing agent; providing an egress out of the space; providing ozone to an atmosphere within the space via the ingress, so as to an atmospheric ozone concentration, as measured at the egress, of at least about 2 ppm; providing hydrogen peroxide to an atmosphere within the space via the ingress, so as to maintain an atmospheric hydrogen peroxide concentration, as measured at the egress, that is at least about 75% by weight of that of the atmospheric ozone concentration; maintaining a relative humidity within the space of at least about 70%; and maintaining a temperature within the space of at least about 15° C.; wherein the steps are conducted substantially simultaneously for a time period of at least about 0.5 hours, whereby the substance is abated.

In an embodiment of the third aspect, the space is selected from an interior of a wall in a building, an interior of a floor in a building, and an interior of a ceiling in a building.

In an embodiment of the third aspect, the atmospheric ozone concentration is from about 2 to about 10 parts per million.

In an embodiment of the third aspect, the atmospheric hydrogen peroxide concentration is from about 75% to about 150% by weight of the atmospheric ozone concentration In an embodiment of the third aspect, the time period is from about 0.5 hours to about 3 hours.

In an embodiment of the third aspect, the ingress and the egress are situated on substantially opposite ends of the space.

DETAILED DESCRIPTION OF THE PREFERRED EMBODIMENT

Figure 1:
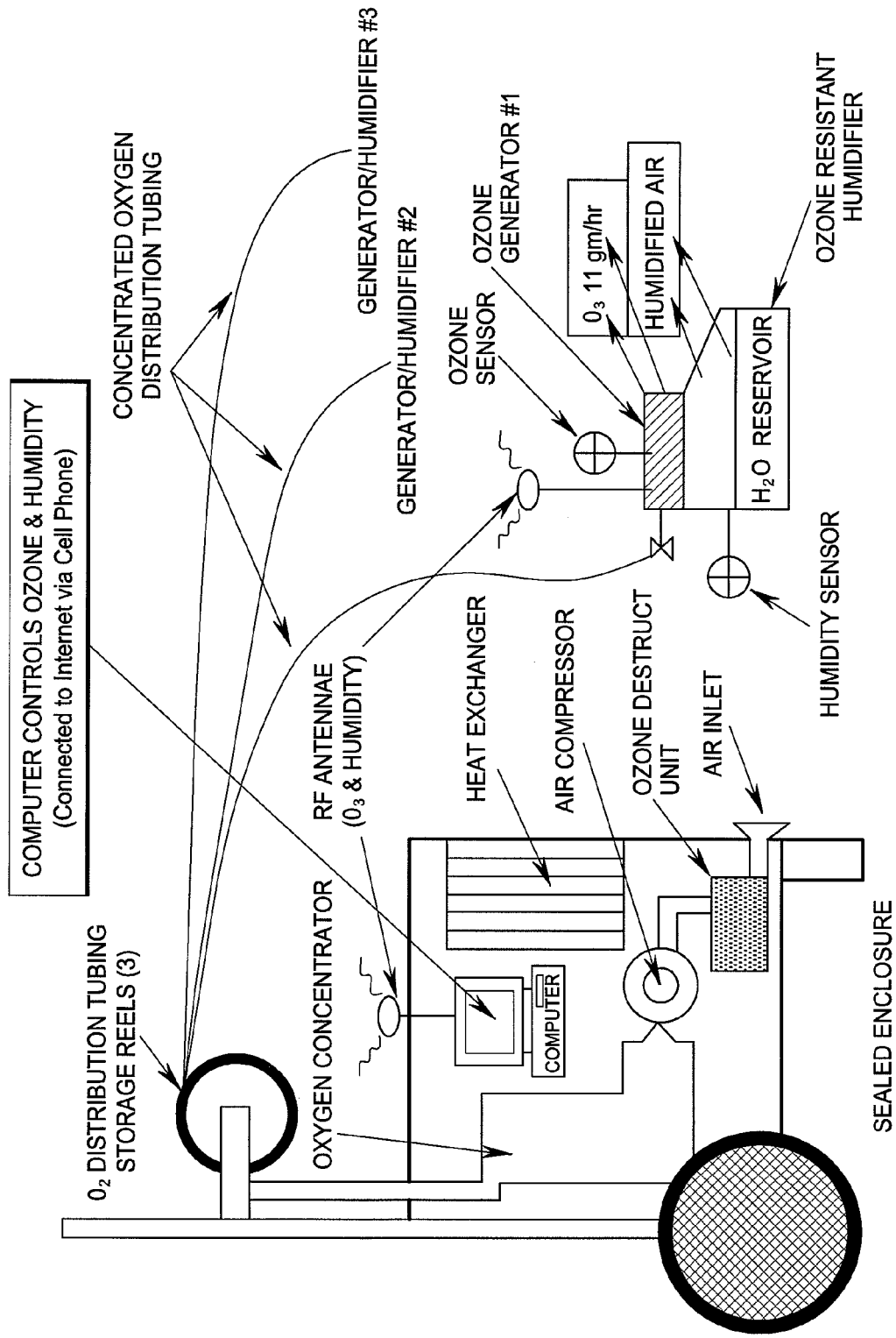
FIG. 1 provides a schematic of an ozone generator and ultrasonic humidifier system capable of delivering ozone at a rate of 60 g/hour.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

The processes of preferred embodiments use high concentrations of ozone. The process involves optimizing treatment conditions by employing a relationship between ozone concentration, humidity, hydrogen peroxide concentration, temperature, duration of treatment, volume of space, and condition being treated. This relationship, termed the 'target dosage' calculation, has been determined by laboratory experimentation and field testing. By utilizing these target dosages to apply a prescribed concentration of ozone and hydrogen peroxide for a prescribed period of time in a controlled area, the elimination of most odors, bacteria, viruses, and molds can be achieved. When the treatment is completed, the ozone generators and humidifiers are removed from the treated area and fans are employed to replace the ozonated air with fresh outside air through just-opened doors and windows. Alternatively the ozone and hydrogen peroxide is left in the space to naturally decompose back to oxygen and water. The half life of ozone is approximately 30 minutes under the conditions employed in this embodiment while the half life of hydrogen peroxide is measured in seconds or minutes when in the presence of ozone. The ozone is thereby returned to a level that is no higher than the outdoor ambient level and the hydrogen peroxide is eliminated completely, resulting in an improvement in indoor air quality.

Ozone has a long history of use in purification methods. The Food and Drug Administration approved ozone for use in food preservation in June 2001. Currently ozone is used to purify most of the tap and bottled water in the US as well as such other diverse tasks as keeping fruits and vegetables fresh during storage. Low powered ozone generators have been available for many years for in-home use; however these units have proven to be very problematic. The units that are safe to operate with people present generate levels of ozone that are too low to be effective in abating mold and other pathogens and allergens. The more powerful units that are effective in decontaminating a room or house generate levels of ozone that are unsafe for continuous occupation.

The concentrations of ozone used in the methods of preferred embodiments can cause lung irritation, so exposure during treatment is avoided. During the process, all animals and people remain outside the area being treated. However, in less than an hour following a treatment, the ozone levels in the area treated can be reduced to that of the outside air and no harmful residual substances are left behind.

The hydroxyl radical, which can be the result of an ozone molecule ($O_3$) interacting with a water molecule (humidity in the air), has been found to be significantly more reactive than direct oxidation by the ozone molecule. However the amount of hydroxyl radicals formed in a mixture of ozone and humidified air is relatively small and is highly dependent on the amount of humidity present. The addition of hydrogen peroxide ($H_2O_2$) to the air greatly increases the hydroxyls formed and therefore greatly increases the speed and efficacy of the methods of preferred embodiments. The hydrogen peroxide reacts with the ozone, converting the ozone and hydrogen peroxide molecules to the more highly oxidative hydroxyl radicals (OH). The resultant mixture then has two methods of eliminating the various contaminants, direct oxidation by the ozone, and indirect oxidation through the action of the hydroxyl radicals. These oxidation reactions compete for contaminants to oxidize. The ratio of direct oxidation with molecular ozone is relatively slow ($10^5$-$10^7$ $M^{-1}sec^{-1}$) compared to hydroxyl radical oxidation ($10^{12}$-$10^{14}$ $M^{-1}sec^{-1}$). In order to maintain the ratio of hydroxyls to ozone as high as possible, hydrogen peroxide is preferably continuously introduced into the area being decontaminated via the ultrasonic humidifier. This ensures the highest concentration of hydroxyl radicals for the entire duration of the preferred embodiment. However, in certain embodiments it can be acceptable to introduce hydrogen peroxide intermittently, or in only a single dose.

The process of the preferred embodiments kills mold it comes into contact with. However, mold that is inside of walls or in other areas not accessible to freely circulating air can necessitate special steps in order to ensure all of the mold is killed.

There is no way to determine how long a treated premises will remain contaminant free. Mold can be effectively abated by the methods of preferred embodiments. However, if the mold's supply of water is not removed the mold can return. Similar principles apply to other contaminants. As long as they are kept from reentering, the premises remains contaminant free.

While living things, such as people, animals, and sensitive plants are removed from the premises while the house is being treated, the process does not harm anything else, e.g., exposed surfaces such as textiles, carpets, paper, paint, and the like, or household goods such as furnishings or electronics. The treatment does not leave behind a film or residue of any kind, only a clean, fresh interior environment.

Odor-causing agents, e.g., fish, curry, garlic, onion and other stubborn cooking odors, along with smoking and animal odors are easily neutralized or removed from the air, as well as from furniture, bedding, and carpets, by the methods of preferred embodiments. Note that animal smells originating from places where the animal has heavily urinated are not easily cleaned due to the concentration of urine present. It is preferred to pre-treat such stubborn areas with an enzymatic cleaner prior to treatment according to the preferred embodiments.

The methods of preferred embodiments have the major advantage of not requiring tenting of the house, or extreme measures to seal off egresses. The methods are also quick. Typically, five hours is sufficient to treat a typical indoor space of 25,000 cu. ft. or less. An average treatment typically takes five hours to complete, one hour to set up equipment, 3 hours for treatment, and another hour for equipment removal, venting of ozone-containing air, and post treatment evaluation of the premises. However treatments can last from seconds to minutes, hours, or even days, depending on the target dosage.

The method is effective in removing odors associated with volatile organic compounds. However, as noted above, if the source of the odor is not eliminated, the odor can return.

While the method of preferred embodiments is especially preferred for abating mold in residential and commercial buildings, it is also effective in treating other structures, such as boats. Surface mold and fuel odors can be eliminated, along with unpleasant aromas from the bilge and head. The process is particularly successful in taking out the musty smells in motor homes that have been closed up for the season or ones that are experiencing fuel smells or cooking odors. Any closed area or structure that is affected by pathogens, allergens, or undesirable odors can be amenable to treatment according to methods of the preferred embodiments, including cars, trucks, passenger buses, aircraft, train cars, and the like.

It is often preferred to treat a premises according to the methods of preferred embodiments on a regular basis, e.g., monthly, quarterly, semi-annually, or the like, so as to maintain a satisfactory air quality level in the premises and avoid recurrence of mold infestations and the buildup of other allergens such as dust mite feces and pet dander.

Abated Substances

Methods of preferred embodiments can be employed to abate any of the substances discussed herein, but the methods are particularly preferred for pathogens, molds, allergens, and Volatile Organic Compounds (VOCs).

Pathogens that can be controlled by methods of preferred embodiments include, but are not limited to Anthrax (*Bacillus anthracis*); Botulism (*Clostridium botulinum* toxin); Brucella species (brucellosis); Brucellosis (*Brucella* species); *Burkholderia mallei* (glanders); *Burkholderia pseudomallei* (melioidosis); *Chlamydia psittaci* (psittacosis); Cholera (*Vibrio cholerae*); *Clostridium botulinum* toxin (botulism); *Clostridium perfringens* (Epsilon toxin); *Coxiella burnetii* (Q fever); *E. coli* O157:H7 (*Escherichia coli*); Emerging infectious diseases such as Nipah virus and hantavirus; Norwalk virus; Severe Acute Respiratory Syndrome (SARS); Acquired Immune Deficiency Syndrome (AIDS) virus; Human Immunodeficiency Virus (HIV); Epsilon toxin of *Clostridium perfringens*; *Escherichia coli* O157:H7 (*E. coli*); Food safety threats (e.g., *Salmonella* species, *Escherichia coli* O157:H7, *Shigella*); *Francisella tularensis* (tularemia); Glanders (*Burkholderia mallei*); Melioidosis (*Burkholderia pseudomallei*); Plague (*Yersinia pestis*); Psittacosis (*Chlamydia psittaci*); Q fever (*Coxiella burnetii*); Ricin toxin from *Ricinus communis* (castor beans); *Rickettsia prowazekii* (typhus fever); *Salmonella* species (salmonellosis); *Salmonella Typhi* (typhoid fever); Salmonellosis (*Salmonella* species); *Shigella* (shigellosis); Shigellosis (*Shigella*); Smallpox (*variola major*); Staphylococcal enterotoxin B; Tularemia (*Francisella* tularensis); Typhoid fever (*Salmonella Typhi*); Typhus fever (*Rickettsia prowazekii*); *Variola major* (smallpox); *Vibrio cholerae* (cholera); Viral encephalitis (alphaviruses [e.g., Venezuelan equine encephalitis, eastern equine encephalitis, western equine encephalitis]); Viral hemorrhagic fevers (filoviruses [e.g., Ebola, Marburg] and arenaviruses [e.g., Lassa, Machupo]); Water safety threats (e.g., *Vibrio cholerae, Cryptosporidium parvum*); and *Yersinia pestis* (plague).

Common household molds that can be remediated by methods of preferred embodiments include, but are not limited to *Acremonium; Alternaria; Aspergillus fumigatus; Aspergillus niger; Aspergillus* species Var. 1; *Aspergillus* species Var. 2; *Aureobasidium; Bipolaris, Chaetomium; Cladosporium, Curvularia; Epicoccum; Fusarium; Geotrichum; Memnoniella; Mucor; Mycelia sterilia; Nigrospora; Paecilomyces; Penicillium* species Var. 1; *Penicillium* species Var. 2; *Pithomyces; Rhizopus; Sporothrix; Sporotrichum; Stachybotrys; Syncephalastrum; Trichoderma*; and Yeast. Molds need high humidity levels and a surface on which to grow. Common areas for mold growth are garbage containers, food storage areas, upholstery, and wallpaper. Molds also commonly grow in damp areas such as basements, shower curtains, window moldings, and window air conditioners.

Indoor allergens that can be remediated by methods of preferred embodiments include dust mite feces. Dust mite feces are the major source of allergic reaction to household dust. The mites thrive on shed human skin and are most commonly found in bedrooms, where skin cells are abundant. Preventive measures include frequently laundering bed linens in hot water and removing carpets from the room. In some cases, homeowners might have to encase the bed mattress, box springs, and pillows in vinyl covers. Other allergens of animal origin include skin scales shed from humans and animals. Commonly called dander, these are another major allergen. Dander from such animals as cats, dogs, horses, and cows can infest a home even if the animal has never been inside. Rodent urine from mice, rats, and guinea pigs is another allergen. Cockroach-derived allergens come from the insect's discarded skins. As the skins disintegrate over time, they become airborne and are inhaled.

Tobacco smoke, engine exhaust, and similar allergens and odors or odor-causing agents can be abated by methods of preferred embodiments, as can volatile organic compounds from sources such as household products including paints, carpets, paint strippers, and other solvents; wood preservatives; aerosol sprays; cleansers and disinfectants; moth repellents and air fresheners; stored fuels and automotive products; hobby supplies; dry-cleaned clothing, and the like. VOCs include organic solvents, certain paint additives, aerosol spray can propellants, fuels (such as gasoline, and kerosene), petroleum distillates, dry cleaning products, and many other industrial and consumer products ranging from office supplies to building materials. VOCs are also naturally emitted by a number of plants and trees. Some of the more common VOCs include ammonia, ethyl acetate, methyl propyl ketone, acetic acid, ethyl alcohol, methylene chloride, acetone, ethyl chloride, n-propyl chloride, acetylene, ethyl cyanide, nitroethane, amyl alcohol, ethyl formate, nitromethane, benzene, ethyl propionate, pentylamine, butane, ethylene, pentylene, butyl alcohol, ethylene oxide, propane, butyl formate, formaldehyde, propionaldehyde, butylamine, formic acid, propyl alcohol, butylene, heptane, isopropyl chloride, carbon tetrachloride, hexane, propyl cyanide, chlorobenzene, isobutane, propyl formate, carbon monoxide, hexyl alcohol, propylamine, chlorocyclohexane, hydrogen gas, propylene, chloroform, hydrogen sulfide, tertiary butyl alcohol, cyclohexane, isopropyl acetate, tetrachloroethylene, cylohexene, methane, toluene, 1-dichloroethane, methyl alcohol, 1,1,2-trichloroethane, 1,2-dichloroethane, methyl chloride, trichlorethylene, diethyl ketone, methyl chloroform, triethylamine, diethylamine, methyl cyanide, xylene, ethane, and methyl ethyl ketone.

Odors and odor-causing substances that can be abated include skunk odors, urine, pet odors, and the like.

It is generally preferred to subject the substance to be abated or remediated to ozone at the preferred concentrations in the atmosphere as discussed below, generally 2 to 10 ppm, and adjust the length of treatment as necessary to ensure satisfactory kill and/or neutralization levels. Serious mold infestations are generally the most resistant substance to remediate. Treatment times of 1, 2, 3, 4, 5, 6, 12, 24, or 48 hours or more can be employed to ensure penetration of the ozone/hydroxyl mixture throughout the entire mass of a serious infestation and achieve a 100% kill and neutralization. However should it be difficult to have the contaminated premises vacated for these long periods of time, it may be necessary to leave the treatment time at the preferred treatment time (2 to 4 hours) while at the same time increasing the level of ozone and/or hydrogen peroxide. Ozone levels of 20, 30, 40, 50, 100, 200, 400 or more ppm can be desirable along with a proportionate increase of hydrogen peroxide to such that the concentration (by weight) of hydrogen peroxide in the atmosphere is up to about 150% or more of that of ozone in the atmosphere introduced into the area to be treated, preferably from about 75% to about 150%, more preferably from about 85% to about 125%, and even more preferably from about 90% to about 100%. However, in certain embodiments it can be desirable to provide even higher concentrations of ozone.

A treatment time of 2 to 3 hours in the methods of preferred embodiments is generally effective in abating serious mold infestations. However, an individual mold spore is generally killed and neutralized within minutes. Protein based allergens are generally neutralized within minutes. Bacteria are generally killed after an exposure time of minutes or less. Viruses are generally killed after an exposure of less than a minute, typically after exposure times as short as several seconds. Certain molds, bacteria, allergens, and viruses can be more resistant to ozone treatments than others. For example, anthrax spores have a hard coating that is preferably "softened up" by exposure to humidity prior to ozone treatment to ensure that all spores are destroyed by a subsequent ozone treatment. See, e.g., R. G. Rice, Ozone Science and Engineering, Vol. 24, pp. 151-158 (2002). In methods of preferred embodiments, it is generally preferred to employ treatment times of 2 to 3 hours, since such times are generally satisfactory for abating a mold infestation, and well exceed the lower limit of treatment time for substances such as protein-based allergens, bacteria, and viruses. However, when it is desired to abate a particularly virulent pathogen, such as anthrax, it can be desired to employ a treatment time of over 3 hours, for example, a treatment having a duration of 5, 6, 7, 8, 9, 10, 11, 12, 16, 20, 24, 28, 32, 36, 40, 44, 48 hours or more. It is also desirable, when abating a particularly virulent pathogen, to also increase the level of ozone and/or hydrogen peroxide. Ozone levels of 20, 30, 40, 50, 100, 200, 300, or 400 ppm or more can be desirable and the concentration by weight of hydrogen peroxide can be increased to more than 100%, preferably more than 125%, and most preferably more than 150% of the concentration by weight of ozone introduced in the area to be treated. Any suitable combination of increased time, increased relative concentration of hydrogen peroxide, and/or increased ozone concentration can be employed.

The methods of preferred embodiments are generally successful in abating substances that are sourced indoors, for example, a mold infestation, dander from a companion animal living in a house, mite feces, tobacco smoke, volatile organic compounds from newly installed carpeting or freshly painted walls, and the like. Substances from outside sources, such as pollen, automobile or diesel exhaust, and the like, can also be treated using methods of preferred embodiments, but recurring treatments can be necessary as such substances reenter the interior space from outside.

Areas and Materials that can be Treated

Any interior or contained space is amenable to treatment by methods of the preferred embodiments. For example, single family homes, apartment buildings, office buildings, schools, hospitals, post offices, locker rooms, restaurants, ships, trains, buses, airplanes, trucks, recreational vehicles, mobile homes, manufactured houses, cargo containers, and the like are particularly well-suited to treatment. The methods are particularly well suited for use in newly constructed homes, buildings, vehicles, and the like, which generally contain substantial quantities of VOC sources, such as newly-installed carpeting and flooring, fresh paint, adhesives, and the like. Larger enclosed spaces, such as warehouses, barns, chicken houses, and other buildings housing farm animals, grain elevators, factories, hangars, subway systems, air terminals, and the like, can also be treated provided that the preferred levels of ozone, hydrogen peroxide, temperature, and humidity can be attained. In certain embodiments, rather than seal and treat the entire volume of enclosed space, the space can be partitioned so as to maintain the preferred levels of ozone, hydrogen peroxide, temperature, and humidity in areas adjacent to those to be treated. For example, plastic sheeting can be draped over a floor or wall to be treated so as to contain the ozone/hydrogen peroxide and humidity and maintain the temperature adjacent to the treated area.

The methods of preferred embodiments can also be employed to treat materials. Materials that can be treated include any materials that can tolerate exposure to the ozone, hydrogen peroxide, humidity, and temperature conditions of preferred embodiments without suffering damage. For example, clothing, bedding and linens, rugs, mail, packages, documents, furniture, food items, agricultural products such as seeds, grains, cut flowers, produce, fruits vegetables, and live plants, containers and packaging materials, and the like. A suitable chamber can be constructed that can be sealed to maintain conditions of ozone and hydrogen peroxide concentration, humidity and temperature at preferred levels, and the material placed inside that chamber and subjected to treatment. In an automated process, materials can be moved through an airlock and into the chamber for treatment for a suitable time period, and then moved out of the chamber through another airlock. Such automated processes can be particularly well suited for the decontamination of large volumes of mail for pathogens such as anthrax, or the decontamination of animal carcasses or meat products (beef, pork, poultry, seafood, and the like) for pathogens such as *salmonella* or *e coli*. If the treatment chamber is of sufficient size, vehicles such as passenger cars or trucks hauling various cargo, rail cars, and the like can be treated therein.

In another embodiment, it can be preferred to subject a room or space to periodic decontamination, such as a surgical suite in a hospital, a treatment or waiting room in a clinic, a kitchen or a restaurant, a bar or nightclub, a theater, a bingo hall, a meat processing area of a grocery store, or the like. In such embodiments, it is generally preferred to permanently install equipment in a location adjacent to the space to be treated. Such equipment can include a control unit, security devices, an oxygen concentrator, an ozone generator, an ultrasonic humidifier, a hydrogen peroxide source, a heater and/or air conditioner, and a ventilation unit. Prior to treatment at a convenient time (for example, after work hours), the space is scanned to ensure that no personnel are present in the room. Motion detectors, heat detectors, video cameras and the like can be suitable for such purposes. Once the space has been confirmed to contain no personnel, a lock down procedure is instituted to prevent anyone from entering the space during the treatment and to maintain conditions within the space. Treatment is then conducted according to preferred embodiments. After ozone levels have been reduced to acceptable levels, the space is then unlocked. If it is necessary to reduce ozone levels to acceptable levels in rapid fashion, ozone destruct units can be employed. A computer can be employed to control the lockdown and treatment process, as well as the treatment schedule.

Assessment of Conditions

In preferred embodiments, the method typically involves an assessment of conditions in the premises, e.g., pathogen, allergen, or gas levels, followed by treatment with ozone/ hydrogen peroxide. An assessment is typically conducted to discover if a premises (e.g., house, office building, boat, and the like) has a pathogen, allergen, or other problem that can be eliminated by using the abatement methods of preferred embodiments. If it is determined that the problem can be effectively eliminated, abatement can be conducted. It is also recommended that the underlying problem responsible for the mold infestation be identified and eliminated, so as to prevent future infestations. As part of the assessment, mold tests, e.g., tests for specific types of mold can be conducted. Other testing can include tests for VOCs, tests for allergens, tests for pathogens, and the like. Ambient conditions, including temperature and relative humidity, the size of the area to be treated (square footage, volume), can also be measured. During the assessment process, it is preferred to wear appropriate protective gear, e.g., respirators, ear plugs, gloves, foot coverings, clothing coverings, goggles, and the like. For example, when dealing with an extensive infestation of particularly toxic mold, it is generally preferred to wear full hazardous material protective gear. In situations wherein the premises are subject to odors that are unpleasant but not otherwise harmful, a respirator, or no protection at all can be sufficient.

While assessments are typically conducted, in certain embodiments an assessment may not be necessary. For example, when an obvious mold infestation is present, when elimination of odors or allergens is the major impetus behind the treatment, or when the premises are treated on a periodic basis for chronic conditions such as asthma triggered by dust mites, the treatment can be initiated without performing any prior assessment.

Preparations Before Treatment

Before commencing an abatement process or other process according to preferred embodiments, it is preferred to determine the area or volume of the premises to be treated such that the target dosage, the quantity, and type of treatment materials and equipment that is sufficient to complete the abatement process can be determined.

It is preferred to meet with the owner (or occupier) of the building before commencing the abatement process. During the meeting, the process can be explained and the owner can assist in preparations for the abatement process. For example, all individuals, unless provided with appropriate protective gear, are instructed to leave the premises for the duration of the abatement process. Any animals, such as pets, are removed from the premises, and it is preferred to remove plants. It is not necessary to remove fish. Problem areas can be identified for treatment, along with areas that may not be amenable to treatment by the methods of preferred embodiments, or areas wherein a contamination can reoccur if the source of the contamination is not eliminated. Areas not amenable to the preferred methods, due to either the location and/or extent of the infestation, can necessitate more extensive treatment or remediation steps, such as those employed to remove and/or dispose of toxic waste, e.g., procedures similar to those used in asbestos abatement.

Internet enabled Decontamination System

After any assessment, including identification of areas for abatement, and/or preparation, such as removing occupants, animals, and plants from the premises, has been completed, the equipment utilized in the mold abatement or other treatment process can be put in place. Such equipment can include, but is not limited to, oxygen concentrators, ozonators, ultrasonic humidifiers, ionizers, dehumidifiers, portable power generators, air conditioners, air compressors, vacuum systems, fans, sensors, recorders, computers, communication devices, and the like.

Any suitable method or apparatus can be used to generate or provide ozone. Commercially available ozone generators with relatively low output and based on either ultraviolet or corona discharge technology are suitable for use in preferred embodiments. One drawback associated with commercially available generators can include the formation of harmful nitrogen oxides along with the ozone. Particularly preferred, however, is ozone generating equipment that delivers substantially pure (i.e., minimal amounts of nitrogen oxides produced) or pure ozone.

In a preferred embodiment, light weight, high output ozone generators employing UV light are moved into the space to be decontaminated. These generators are preferably under 15 lbs so as to minimize the potential for worker injury. They employ sensors which detect their current state of operation and this on-off state is relayed to the accompanying computer control center via a localized wireless system. Along with the generators, an ultrasonic humidifier or humidifiers and computer control center are also carried into the space to be treated.

In decontaminating very large spaces such as commercial or industrial buildings, corona discharge ozone generators employing oxygen concentrators may be used to deliver highly concentrated quantities of ozone to the space. Oxygen concentrators are typically heavy, requiring them to be moved about on a cart to prevent worker injury. Therefore, the oxygen concentrator can be maintained in a convenient location, such as in a van or on a truck used to transport equipment utilized in the treatment process, and the pure oxygen is then delivered from a location to any number of ozone generators in remote locations via piping. In other embodiments it can be desirable to have all equipment, including the oxygen concentrator, placed within the dwelling during the treatment process. In an industrial setting or hospital setting wherein treatments are administered on a regular basis, it can be preferable to permanently install the oxygen concentrator.

The computer control center is typically enclosed within an environmentally sealed case. The computer control system can perform any number of functions. It can communicate via radio or other signals (wireless) or via a communication line (wire or fiber optic) with remotely located equipment including ozone generators as well as sensors monitoring ozone concentrations, humidity and temperature. With this information, the computer can control dosage to that indicated by research data covering target dosages for any given situation. The target dosage is typically selected via a look-up table stored in the computer's memory or storage unit that provides optimal ozone dosages for a particular combination of humidity, temperature, and condition being treated. As a further adjunct, ultrasonic humidifiers or dehumidifiers can preferably be connected to the system, permitting the control of ambient humidity levels while at the same time introducing hydrogen peroxide into the area being treated.

An additional function of the computer control center can include communicating with the technician performing the treatment and a remote office location via a combination of cell phone and Internet technology. Each treatment system can have its own Internet address and communication can be established with the system from anywhere in the world as long as the system is in range of a cell phone tower. Alternatively, the system can be connected to an existing phone line or internet connection in the premises to be treated, permitting access to the internet, or dial-up access to a secure computer system in the remote office location.

An additional function of the computer control center can include a Global Positioning System (GPS) transmitter which will be used to communicate the position of the computer thereby allowing the technician and the company employing the technician to track the computer control system at all times.

Power to the system can be provided from a dedicated generator or battery, or the system can utilize existing utility outlets in the premises to be treated.

In a preferred embodiment suitable for use in typical residential settings, the system features include a number of light weight, high output, hand carried UV based ozone generators (number dependent on volume and pollutant to be treated), one or more ultrasonic humidifiers with built in humidity control devices and reservoirs capable of containing a water/hydrogen peroxide mixture, computer control center, manual temperature and humidity sensors, distribution/evacuation fans, power generator (as necessary) and ozone destruct unit (as necessary)

In another embodiment suitable for use in typical residential settings, the dosage is calculated manually and the equipment consisting of ozone generators, one or more ultrasonic humidifiers with built in humidity control devices and reservoirs capable of containing a water/hydrogen peroxide mixture, manual temperature and humidity sensors, distribution/evacuation fans, is placed in the residence and the decontamination period is controlled by the technician according to the manually calculated dosage.

In a preferred embodiment suitable for use in typical larger commercial or industrial settings the system features include the following: cart mounted oxygen concentrator, computer control center, ozone destruct unit, heat exchanger, air compressor and cell phone communication unit; up to 5 hose reels and holders for oxygen distribution hoses; up to 5 ozone generation units with ozone sensors; up to 5 ultrasonic humidifiers with water reservoirs capable of containing aqueous hydrogen peroxide, up to 5 humidity sensors; up to 5 radio wave send/receive units.

The oxygen concentrator carried on the cart case generates and supplies highly concentrated oxygen to the remotely located ozone generators. The cart mounted reels preferably hold up to 100 feet of ¼ inch vinyl tubing which carries the concentrated oxygen to the ozone generators strategically located throughout the premises being decontaminated. Any suitable tubing can be used, provided it is substantially inert to ozone or oxidation, such as stainless steel tubing, inert plastic tubing, or the like. To prevent premature failure due to the corrosive properties of ozone, only non-ozonated air can be used to supply the oxygen concentrator. An ozone destruct unit is preferably mounted in the concentrator's inlet air supply. This unit eliminates the ozone in the concentrator's air supply and greatly prolongs the life of the unit. As further protection, the cart case can house a heat exchanger to ensure that temperatures within the unit remain below the temperature specification limits set by the concentrator's manufacturer.

As previously mentioned, sensors mounted on the ozone generators will detect ozone, humidity and temperature levels. Ozone generation will be regulated according to the required target dosages for the particular problem being treated. Dosage tables generated by laboratory experimentation and further adapted through field-testing are used to determine optimal dosage levels. These dosage tables are stored in the computer and used to calculate the ozone/hydroxyl levels, humidity, and time required to complete specific decontamination tasks. While it is generally preferred to employ a computer to determine the proper ozone, humidity, and temperature levels, any suitable method can be employed. For example, manual calculations can be performed, or a printed look-up table can be employed. An advantage to using a computer is that levels can be rapidly determined and adjusted as needed if ambient conditions change over the course of treatment. Changes in dosages over time can also be conveniently tracked. FIG. 1 provides a schematic of a preferred ozone generator and ultrasonic humidifier system capable of delivering ozone at a rate of 60 g/hour along with hydrogen peroxide at a concentration by weight that is about 75% to about 150% of the ozone concentration to be delivered.

In preferred embodiments, operation support is provided via several systems, including technician training, providing equipment, delivering treatment, providing technical data, and maintaining customer and technical databases. Technician training typically includes detail on how the service is performed, gives some detail on ozone, hydrogen peroxide, ozone generators, ultrasonic humidifiers, sensors etc., with a strong emphasis on safety; training in all aspects of sales and customer relations; specific details on equipment operation, sensors, safe operation and maintenance of vehicles, and the like, as well as more detail on the chemistry behind the process; legal, moral and ethical aspects of dealing with customers and representing the company; detailed explanation of existing sales and marketing programs and how the technicians are involved in these programs; functional aspects of the sales and operations databases as well as efficient scheduling; business training for those who may, in the future, be operating a central office location; and details on accounting, legal, personnel management, and other responsibilities.

Equipment for residential and small commercial treatment typically includes fully equipped trucks or vans. Each truck or van is preferably equipped with sufficient ozone generating equipment to service 2 to 4 jobs per day, depending upon the size of the premises and the contaminant involved. The trucks and vans are equipped with all necessary safety gear to ensure that neither the technicians nor the customers are endangered in any way. The trucks and vans also have small coolers in which to transport samples (e.g., mold spores) and a laptop computer equipped with the appropriate software and which is updated daily with the appropriate work orders and customer information. Once at the job site, the technicians use the laptop computers to collect any job-related information desired, including, but not limited to, volume and/or area treated, ozone concentration levels, temperature, humidity, customer comments, technician comments, and the like. The laptops can be directly connected to a main computer system through the Internet or through landlines. This allows automatic updates of databases, immediate notification of scheduling changes, and updated customer information as well as identification of the current location of the service truck.

Incoming calls from prospective customers are preferably managed in a highly professional manner through a centralized call center. Standardized phone protocol is utilized, emphasizing courtesy while obtaining all pertinent information as quickly as possible. When necessary, the call center can provide a description of the service as well as respond to a host of frequently asked questions (FAQ's). The first image of the company is the courtesy and professionalism of the voice on the line. Telephone closing techniques as known in the art can be used when appropriate by company representatives.

In certain preferred embodiments, lead development information is collected and loaded into the company's sales and marketing database. Any suitable database software can be used, however, it is preferred that the software be Internet compatible, i.e., the database can be updated and/or modified via the Internet. The program accumulates contact information, for the purposes of tracking contacts, their histories, and pending actions. It is accessible on-site or from remote locations. The system is also used to produce automated direct marketing campaigns. The system is fully capable of expanding to accommodate business growth and is integrated with the technical database software that has been installed. The database is preferably customized to better function as a technical database for use in the preferred embodiments. It can be customized to produce work orders, invoices and to accumulate each job's technical data including tests results, treatment data, and customer reactions. This software allows a database to be built on efficacy of the process in different conditions and with different types of contaminants.

Any suitable computer network can be employed in those embodiments wherein a computer is desirable for some aspect of the treatment or subsequent data storage or analysis. A computer network based on a T1 backbone and server running MS 2000 Server software available from Microsoft Corporation is utilized in a preferred embodiment. The system has full security and is set up as a Virtual Private Network (VPN) allowing authorized users access from any Internet connection. This also allows the technicians the capability of accessing the network from home or any other location with Internet access.

Pretreatment

In certain embodiments, it can be desirable to pre-treat the area prior to subjecting the area to ozone treatment. A preferred pretreatment involves subjecting the area to be treated with humidity. Certain pathogens, such as mold spores and anthrax, are resistant to conventional ozone treatment. The anthrax bacterium, for example, possesses a hard shell that resists penetration by ozone. By subjecting anthrax to humidity prior to ozone treatment, the ozone, and/or hydroxyl is better able to penetrate the microorganism and destroy it. Likewise, mold spores are resistant to penetration by ozone, but can be made more amenable to treatment by first subjecting them to humidity. Treatment of VOCs is also facilitated by humidity. Ozone reacts with the atmospheric water and hydrogen peroxide to produce reactive hydroxyl groups, which then react with certain VOCs to yield less harmful or harmless substances.

When the material to be treated includes molds, a pretreatment consisting of exposure to a relative humidity of 70% to 95% is typically employed. Typical pretreatment exposure times of 10 minutes, 15 minutes, 30 minutes 45 minutes, 1 hour, 1.5 hours, 2 hours, 2.5 hours, 3 hours, 4 hours, or more can be employed, depending upon the substances to be abated and the nature of the space or material to be abated. In residential mold remediation, pretreatment times of from 30 minutes to 2 hours are generally preferred. In decontaminating a material infested with anthrax, pretreatment times of from 12 hours to 24 hours are generally preferred.

Abatement of Living and Working Spaces

If the area to be treated has an air duct system (e.g., heating or heating/air conditioning system), it is preferred to position one or more ozonators and humidifiers adjacent to the return air inlet. Typically, for treating volumes of 25,000 cu. ft. or less, it is preferred that at least 10 g/hr of ozone is drawn into each air inlet. However, in certain embodiments satisfactory results can be obtained at a lower level of ozone generation, for example, at about 0.1, 0.5, 1, 2, 3, 4, 5, 6, 7, 8, or 9 or more g/hr. Likewise, in certain embodiments a higher level of ozone generation can be preferred, for example, about 10, 11, 12, 13, 14, 15, 20, 25, 30, 40, 50, 60, 70, 80, 90, or 100 or more g/hr. Along with the higher level of ozone generation is a proportionately higher level of hydrogen peroxide introduction, generally at a concentration by weight that is 75% to 150% of concentration by weight of ozone provided. Commercially available ozonators are available in a variety of sizes. Size is generally reported in terms of ozone output in grams/hour. It is generally preferred to locate mid-sized (e.g., 6.10 or 15 gm/hr) ozonators in larger areas, e.g., living room, kitchen/family room, open stairways, open office spaces, and the like. Smaller ozone generators (e.g., 1-5 gm/hr) are preferably situated in small or closed-in areas, or areas that are unlikely to get circulating air, for example, basements, storage areas, and the like. Generally dosage calculations show that ozone generators that are capable of generating 60 g/hr of ozone are sufficient to treat a 2,000 sq. ft. house with forced air ducting. More ozone can be preferred for a house without forced air ducting. Typically, dosage calculations show that one gram of ozone per hour is preferably delivered for every 250 cu. ft. of area to be treated. More or less ozone can be desirable, depending on humidity, temperature, and specific condition being treated. Therefore, for each 1 gm/hr of delivered ozone, an area of 33 sq. ft. with 8 ft ceilings can be decontaminated. Determination of the amount of ozone required is made according to the target dosage found in the dosage tables relating time of treatment to the ozone concentration, delivered hydrogen peroxide, humidity and temperature to the problem be treated such as mold, allergens, pathogens or VOCs.

After the ozone generators are situated and turned on, the forced air system is then turned on to circulate the air. It is generally preferred that no heating or cooling of the air is conducted, however, in certain embodiments it can be preferred to heat or cool the air so as to obtain optimal abatement results.

Humidity is a significant factor in the kill rate of allergens and pathogens. In general, the higher the humidity, the faster the ozone kills the pathogen or destroys the allergen. While not wishing to be bound to any particular theory or mechanism, it is believed that the ozone reacts with the water vapor forming hydroxyl radicals thereby increasing the effectiveness of the process. Generally, it is preferred that the relative humidity in the premises to be treated be at least 30% or more, preferably the relative humidity is at least 40%, 45%, 50%, 55%, or 60% or more, more preferably the relatively humidity is from 65% to about 70%, 75%, 80%, 85%, or 90% and most preferably the relative humidity is from about 70% to about 90% or 95%. Relative humidities greater than 95%, especially relative humidities of 100%, are generally not preferred due to the risk of condensation, which can lead to bleaching of sensitive materials. However, in certain embodiments relative humidities greater than 95% can be acceptable if sensitive materials are not a concern. In order to ensure that there is adequate formation of hydroxyl radicals, specifically at low humidity levels, hydrogen peroxide is preferably supplied to the area being treated at a concentration by weight that is up to about 150% or more (preferably about 75% to about 150%) of the concentration by weight of ozone being delivered. For example, if the area is being treated with about 60 g/hr of ozone, then from about 45 to 90 g/hr of hydrogen peroxide is also delivered. At low humidities, and for the abatement of particularly virulent pathogens, it is generally preferred to employ higher relative concentrations of hydrogen peroxide, preferably greater than 100%, 125%, or 150% or higher.

In coastal areas, ambient humidity can provide optimal results. In these situations the ultrasonic humidifiers are used only to deliver a minimal amount of hydrogen peroxide. However, in desert areas or under low humidity conditions (e.g., winter in northern areas of the United States), it can be preferred to increase the humidity via one or more ultrasonic humidifiers so as to achieve optimal results. Once treatment is completed, it may be desired to employ one or more dehumidifiers to rapidly restore the ambient humidity to the treated premises, if the premises are humidity-controlled. In certain instances, it may not be feasible to humidify the area to be treated. For example, the area can contain humidity-sensitive materials (e.g., antiques, rare books, old documents, fragile textiles or wallpaper and the like). In those instances, treatment can be conducted under ambient humidity conditions with the addition of hydrogen peroxide, but the duration of the ozone treatment can be extended to ensure satisfactory results. However under these conditions it can be desirable to increase the ratio of delivered hydrogen peroxide to ozone from 150% to 200%, 250%, 300%, 350%, 400%, or even 1000% or more of the concentration by weight of ozone present. Any suitable schedule of introducing ozone, moisture, and/or hydrogen peroxide can be employed, e.g., constant introduction of one or more of ozone, moisture, and hydrogen peroxide, intermittent introduction of one or more of ozone, hydrogen peroxide, and humidity, varying concentrations, varying temperatures, and the like.

Temperature levels also correlate with the effectiveness of the treatment method in killing mold. Generally, as temperature increases, the effectiveness of the treatment increases. However the amount of ozone required to achieve and maintain the target dosage also increases as the ozone more readily reverts back to oxygen at higher temperatures (i.e., ozone exhibits a shorter half life at higher temperatures). Generally, it is preferred to conduct the treatment at a temperature typically considered a "room temperature," namely about 17.7° C. (64° F.), 18.3° C. (65° F.), 18.8° C. (66° F.), 19.4° C. (67° F.), 20° C. (68° F.), 20.5° C. (69° F.), or 21.1° C. (70° F.) up to about 21.6° C. (71° F.), 22.2° C. (72° F.), 22.7° C. (73° F.), 23.3° C. (74° F.), 23.8° C. (75° F.), 24.4° C. (76° F.), 25° C. (77° F.), 25.5° C. (78° F.), 26.1° C. (79° F.), 26.6° C. (80° F.), 27.2° C. (81° F.), 27.7° C. (82° F.), 28.3° C. (83° F.), 28.8° C. (84° F.), or 29.4° C. (85° F.). In most residential and commercial settings, the ambient temperature falls within this range. However, if the premises to be treated is not equipped with heating or air conditioning, it can be preferred to adjust the interior temperature prior to initiating treatment, or to control the temperature at a pre-selected level during treatment. When the ambient temperature is high and the structure to be treated is not equipped with air conditioning, an air conditioning unit can be provided as part of the equipment system and used to cool the temperature, e.g., down to below 29.4° C. (85° F.). Cooling the interior to below 17.7° C. (64° F.) generally results in only an incremental reduction in the rate of ozone decomposition. Thus, it is generally not preferred to cool the interior below this temperature. If the ambient temperature is substantially below 17.7° C. (64° F.), it is generally preferred to heat the interior. In certain conditions, the temperature in the structure to be treated can be controlled to a pre-selected temperature, for example, a cold storage locker or a room containing equipment or machinery that must be operated at an elevated or reduced temperature. Under such conditions, the treatment is preferably conducted at ambient temperature and the ozone level and/or humidity is adjusted to achieve optimum results. In certain embodiments, however, it can be desirable to treat an area at temperatures outside of those typically considered ambient temperatures. For example, a refrigerated unit maintained at a temperature above 0° C. (32° F.) can be satisfactorily treated by adjusting the humidity, hydrogen peroxide, and ozone levels. Generally, ozone levels are increased at low temperatures. However, lower ozone levels of 2 to 10 ppm can be employed in conjunction with a longer treatment time.

Ozone levels of 2 to 10 ppm are generally preferred for treating mold and other contaminants. However, in certain embodiments it can be preferred to employ ozone levels of 1.9, 1.8, 1.7, 1.6, 1.5, 1.4, 1.3, 1.2, 1.1, 1.0, 0.9, 0.8, 0.7, 0.6, 0.5, 0.4, 0.3, 0.2 ppm or less. In other embodiments, ozone levels of 11, 12, 13, 14, 15, 16, 17, 18, 19, 20, 25, 30, 35, 40, 45, 50 ppm or more can be preferred. At optimal hydrogen peroxide, humidity, and temperature levels, a longer treatment time is preferably employed at reduced ozone levels and a shorter treatment time is preferably employed at higher levels so as to ensure a satisfactory kill and/or neutralization level.

In terms of the optimal combination of ozone level, hydrogen peroxide, temperature, and humidity, it is generally preferred to conduct a treatment at a temperature of about 21.1° C. (70° F.), a relative humidity of about 85%, a hydrogen peroxide addition of 107% by weight of ozone, and an ozone level of about 10 ppm. Under these conditions, the length of time required to achieve a 100% kill for mold spores is minimized. For in a typical residential setting, a 100% kill can be achieved in about 3 hours or less. When the temperature ranges from about 15.5° C. (60° F.) to about 26.6° C. (80° F.), i.e., interior temperatures typically observed for residential and commercial buildings, it is preferred that the relative humidity be in the range of about 70% to about 85%, and the ozone levels be in the range of about 2 ppm to about 10 ppm (with a corresponding hydrogen peroxide concentration by weight of 75% to 150% of that of the ozone concentration by weight). Under these conditions, the optimal time to achieve a 100% kill is typically about 1 to about 3 hours.

For structures situated in high humidity environments, e.g., the coastline, the Midwest during summer, and the like, wherein the relative humidity ranges from about 85% to about 95% and ambient temperatures range from about 21.1° C. (70° F.) to about 32.2° C. (90° F.), lower ozone levels can be employed. Under these conditions, the optimal time to achieve a 100% kill is typically about 1 to about 3 hours.

For structures situated in low humidity environments, e.g., desert communities, and the like, wherein the relative humidity ranges from about 5% to about 20% and ambient temperatures range from about 23.8° C. (75° F.) to about 37.7° C. (100° F.), it is preferred that the relative humidity is raised via the use of an ultrasonic humidifier or other suitable method to from about 70% to about 85% before beginning treatment and that the ozone levels are in the range of about 2 ppm to about 10 ppm. Under these conditions, the optimal time to achieve a 100% kill and/or neutralization is typically about 1 to about 3 hours. If it is not feasible to raise the humidity levels to the 70% to 85% range, then a higher level of hydrogen peroxide can be introduced to ensure the production of sufficient hydroxyl radicals to complete the decontamination process. Hydrogen peroxide levels of 125% to 150% of the weight of introduced ozone can generally be used to ensure decontamination. However under the most extreme conditions it may be desirable to increase the ratio of delivered hydrogen peroxide to ozone from 150% to 200%, 250%, 300%, 350%, 400%, or even 1000% or more.

In commercial and residential settings, and the like it is preferred to open all closet and cupboard doors, and to move items stored in cupboards and closets to facilitate air circulation. Doors, windows, fireplace dampers, and other air egresses are preferably closed.

In residential settings, if dust mites are problematic, it is preferred that all linens be taken off beds and washed in 60° C. (140° F.) water. Mattresses are typically removed from the box spring and leaned up against the box spring so as to facilitate air circulation around the mattress. If feasible, blankets, pillows, and bed spreads are preferably placed in a manner that allows satisfactory air circulation. Exhaust fans, e.g., in the kitchen, bathroom, and the like, are turned on, which helps ensure that ozonated air reaches the outlet ducting of these areas. If such fans have a variable speed, they are preferably operated at their lowest possible level to reduce the amount of ozone that will evacuated while at the same time ensuring that the vent system is decontaminated.

Before the ozonators are activated, ultrasonic humidifiers may be employed to achieve required relative humidity levels and to deliver the hydrogen peroxide in prescribed amounts according to the target dosage. Once target humidity levels are achieved, the area can be evacuated of any nonessential personnel. For those individuals remaining in the premises, a respirator (and goggles if the respirator is not a full-face respirator) is preferably in place before turning on the ozonators. The ozonators and humidifiers supplying hydrogen peroxide are typically turned on starting with the most remote areas of the premises and finishing with the heating and air conditioning inlet or inlets last. After the ozonators have operated for a short time period, typically about ten minutes, it is preferred to test and record ozone, temperature, and humidity levels. For non-automated ozonators this will require reentering the premises and taking the necessary readings. Once the ozone and humidity levels have reached target dosage levels, typically at least about 2 to 10 ppm ozone and 50-90% RH, effective treatment has begun, and the premises can be left closed for the duration of the treatment. Although 2 to 10 ppm ozone is generally preferred, in other embodiments a higher or lower ozone level can be desirable, e.g., less than 0.1, 0.5, 1, 2 ppm ozone up to about 15, 20, 30, 40, 50, 60, 70, 80, 90, 100, 500, 1000, 2000, 3000, 4000, 5000 ppm ozone or more. For these higher levels of ozone, proportionately higher levels of hydrogen peroxide are also generally preferred, again based on the 75% to 150% hydrogen peroxide to ozone by weight. If the contamination is particularly extensive or the mold to be abated particularly toxic, higher ozone levels can be preferred. To prevent injury, all doors and other possible entrances to the building are preferably locked and caution signs placed the entrances.

Humidity, temperature, and ozone concentration readings are typically recorded in each room during the course of the treatment procedure. These recordings can be obtained automatically, e.g., by stand-alone recorders in the rooms or by the ozone generator equipped with measuring devices. Alternatively, the recordings can be obtained manually at pre-selected intervals.

Treatment is typically continued for up to 48 hours depending on the target dosage which relates temperature, humidity, ozone concentration, and condition being treated to treatment time. After treatment is completed, the ozonators and humidifiers are turned off and ozonated air can be evacuated from the premises if immediate occupancy is desired. Alternatively the ozone can be left to degrade back to oxygen if immediate occupancy is not required. If immediate occupancy is desired fans are typically placed in one or more doorways and/or windows to blow ozonated air out of the premises. High volume fans (9400 c.f.m.) are generally preferred for residential applications; however fans capable of moving more air or less air than 9400 c.f.m. can also be suitable for use. The evacuation fans are typically operated for 30 minutes, and then ozone levels are tested, especially in areas where circulation from the fans is lowest, such as bedrooms, basement, and the like. Depending upon the circulation efficiency, longer or shorter operation times can be preferred.

As an alternative to the use of evacuation fans, the premises can remain closed and the ozone can dissipate and/or decompose to safe levels without taking active steps to remove ozonated air from the premises. In an enclosed space with poor air circulation, ozone levels will typically return to ambient levels after about 6 hours. However, it is generally preferred to take active measures to evacuate ozonated air such that the delay in reoccupying the premises is minimized.

Ozone levels are periodically tested until a pre-selected ozone level at which it is safe to reoccupy the building is achieved. A self contained breathing apparatus or respirator is preferably employed for testing until a level of 0.1 ppm ozone, 0.05 ppm ozone, or less is recorded, or until levels of ozone similar to outside ambient levels are achieved, if ambient levels are higher than 0.1 or 0.5 ppm. An ozone level of 0.05 ppm has been determined by the FDA to be a safe level for continuous exposure. An ozone level of 0.1 has been determined by OSHA to be safe for exposure times of up to 8 hours. Once the level drops below 0.05 ppm or outside ambient levels, the treated area is typically safe for reoccupation by people, animals, and plants and treatment is complete. If level is not below 0.05 ppm in all areas, circulation by fans is continued until this level is reached. While 0.05 ppm is the preferred level deemed safe for reoccupation, in certain embodiments it can be preferred that a lower level be attained, e.g., a level characteristic of ambient ozone levels prior to treatment. Alternatively, a higher level of ozone can be acceptable in certain embodiments.

Ozone levels can be tested using commercially available instrumentation, such as that manufactured by Eco Sensors of Santa Fe, N. When testing for current ozone levels, the instrument is used in accordance with the manufacturer's instructions. These typically include allowing adequate warm up time (generally at least 5 minutes), not blocking the air flow into the instrument while testing, making all measurements in still air as moving air can affect the readings, keeping the instrument away from the body as body odors can bias the reading, not using the instrument to take measurements directly from the outlet of the ozonators which can result in incorrect readings and/or damage to the instrument.

After the premises has been deemed safe for reoccupation, doors and windows can be unlocked, caution signs can be removed, and all equipment, including fans, ozonators, and humidifiers can be removed from the premises.

It is noted that in the case of allergens and pathogens, treatment does not remove the allergen or pathogen from the treated area. In the case of a pathogen, such as mold spores, the organism is killed. If the pathogen has an ability to produce an allergic reaction, this ability is also neutralized. In the case of an allergen such as animal dander or dust mite feces, the protein causing the allergic reaction is neutralized by the ozone treatment such that it is unable to cause an allergic reaction. A subsequent cleaning step to remove the dead organism or deactivated allergen can be desirable in certain embodiments, but is not necessary.

Pretreatment and Post-Treatment for Ozone Control

After an ozone treatment is administered and ozone returns to ambient levels, a strong ozone odor can still be noticeable. If there is such an odor, it is generally associated with closets and bedrooms. While not wishing to be bound to any particular theory, it is believed that fabrics or other materials containing natural or synthetic fibers having an electrostatic charge can attract and hold ozone, slowly releasing it back into the surrounding air at safe but noticeable levels. While a large portion of the population considers ozone to have a pleasant odor, some individuals consider the odor unpleasant. Other individuals, typically those suffering from asthma, can find ozone to be an irritant. Accordingly, a method for reducing or eliminating lingering ozone or the odor associated with ozone is desirable.

Any suitable method can be employed for destroying or removing lingering ozone. For example, ultraviolet (UV) light is preferably employed. A UV light source can be brought into the space treated, and the light therefrom can be passed over the materials that are holding the ozone, such as bedding, clothes, drapes, and the like. The UV treatment is preferably conducted after completion of the ozone treatment, most preferably as soon as detected ozone levels reach ambient levels.

Removal of ozone can also be accelerated by subjecting the interior spaces to elevated temperatures, for example, by a radiant heater or hot air blower.

In other embodiments, it can be preferred to employ ions. Depending upon the nature of the materials in the treated space, it can be desirable to employ only positive or negative ions, or to employ positive ions for a time followed by negative ions, or vice versa. Any suitable equipment for generating ions can be employed. It is generally preferred to employ an ion generator capable of producing $1 \times 10^{12}$ ions per second (negative or positive). Such an ion generator is generally suitable for use in rooms or spaces having an area of approximately 500 sq. ft. Alternatively, bipolar ionization can be employed. Bipolar ionization uses an alternating current to produce both positive and negative ions. Bipolar ionization utilizes a process involving association and disassociation to generate a highly reactive mixture of ionized gas consisting of atoms, molecules, and free radicals capable of creating chemical changes. There are several types of devices that can be used for this process. For HVAC applications, a non-thermal type of surface discharge reactor is preferably used. Bipolar ionization was first used commercially in 1972 in the food and meat industry in Western Europe to improve shelf life of perishable foods with limited or no mechanical refrigeration.

When the bipolar ion generator is connected to an oscilloscope, a sinusoidal waveform is observed. On one side of the waveform, the bipolar generator produces positively charged ionized gas molecules and on the other side of the waveform, the bipolar generator produces negatively charged ionized gas molecules. This is a pulsed AC system, which alternately produces negative and positively ionized gas molecules. In operation, a pulsed ion field is created in the vicinity of the bipolar generator. As air passes through the ion field, electrons in the valence shells of stable molecules receive excitation energy. As the air stream moves out of the ion field and through the air-handling unit, the electron vibrational energy permits valence electrons to overcome nuclear attraction and escape. Chemical bonds are broken in gas molecules, ionic compounds disassociate to positive and negative ions, and covalent compounds disassociate to free radicals. In the absence of a polar field, the highly unstable ions and free radicals combine to form more stable compounds.

To determine what type or types of ions are preferred for treating a space, the materials contained within the space can be classified on the basis of their place in a triboelectric series. Below is a very short triboelectric series that provides an indication of the ordering of some common materials. A material that charges positive will be the one that is closer to the positive end of the series and the material closer to the negative end will charge negatively. Accordingly, to reduce the charge on the material, ions of opposite polarity can be applied. It is the work function of the material that determines its position in the series. In general, materials with higher work function tend to appropriate electrons from materials with lower work functions. Triboelectric series (from positive to negative): positive (+)>asbestos>glass>nylon>wool>lead>silk>aluminum>paper>cotton>steel>hard rubber>nickel & copper>brass & silver>synthetic rubber>Orlon>saran>polyethylene>Teflon>silicone rubber>negative (−). While such triboelectric series can be helpful in determining the preferred ion treatment, other factors can affect the preferred treatment. For example, real materials are seldom very pure and often have surface finishes and/or contamination that strongly influence triboelectrification. The spacing between materials on a triboseries does not allow one to predict with any confidence the magnitude of the charge separated. Many factors besides the difference in the electronic surface energy, including surface finish, electrical conductivity, and mechanical properties, can also strongly influence results.

In addition to controlling ozone odor, bipolar ionization methods can yield additional benefits, including microbiological control, control of other odors and gas phase chemicals, static control, and filtration enhancement. After dissipating the ionization energy, air with a balanced electrical charge remains. In the absence of any electrical charge, submicroscopic particulates are not attracted to foreign surfaces and remain airborne and naturally buoyant. Air currents established by an efficient air distribution system displace the particulates and carry them back to the filters in the air-handling unit. Particulates that pass through the filters remain buoyant on subsequent circulation cycles and are returned to the filters for another attempt at removal. With every pass through the filters, the probability increases for removal.

It is generally preferred to employ an ion treatment during the ozone treatment. However, an ion treatment can also be conducted before or after the ozone treatment, or at any suitable time.

Remediation of Norwalk Virus

Interior spaces, such as in cruise ships, infected with Norwalk virus can be remediated by methods of preferred embodiments. The procedure generally preferred is as follows: Ships are generally constructed such that sections of the ship can be isolated from the remainder of the ship. These sections have independent heating, ventilating, and air conditioning systems (HVAC) as well as sealable doors providing total isolation. Humidification and ozonation equipment can be brought aboard the ship and placed within one or more of the isolatable sections. The ultrasonic humidifiers and ozonators can be placed near or within the air inlets of the HVAC system and all systems placed in operation. This circulates the ozone, hydrogen peroxide, and humidity throughout the isolated section of the ship at target dosages determined to be lethal to the Norwalk and other viruses and bacteria. Once the target dosage has been achieved then the ozone can be left to decompose back to oxygen or it can be evacuated by opening the outside makeup air system to allow 100% makeup air, thereby evacuating the ozone and allowing rapid reoccupation of the treated section.

Remediation of Anthrax

Methods of preferred embodiments are suitable for use in decontaminating indoor areas or materials contaminated with anthrax. The procedure generally preferred is similar to that noted for Norwalk virus, with the exception that the area to be treated is pre-treated with humidity for a period of 12 to 24 hours at levels of humidity greater than 70%. Ultrasonic humidifiers are placed within the area to be treated. They are turned on and allowed to operate until such time as a level of at least 90% relative humidity is achieved. Once this level has been achieved, the pretreatment period has begun. Once the pretreatment period has been concluded, the actual treatment can be completed based on target dosages for anthrax. Target dosages for anthrax require that the amount of hydrogen peroxide relative to ozone introduced via the ultrasonic humidifiers to the treatment area is higher than in other decontamination situations, preferably at least from about 125 to 150%, but in certain embodiments even higher. With regard to safety issues, significantly more stringent safety procedures are required when treating an area contaminated with anthrax or other particularly virulent pathogens. Scientifically accepted hazardous material safety procedures are followed strictly by all personnel involved in the decontamination procedure.

EXAMPLE

Santa Monica House

Figure 2:
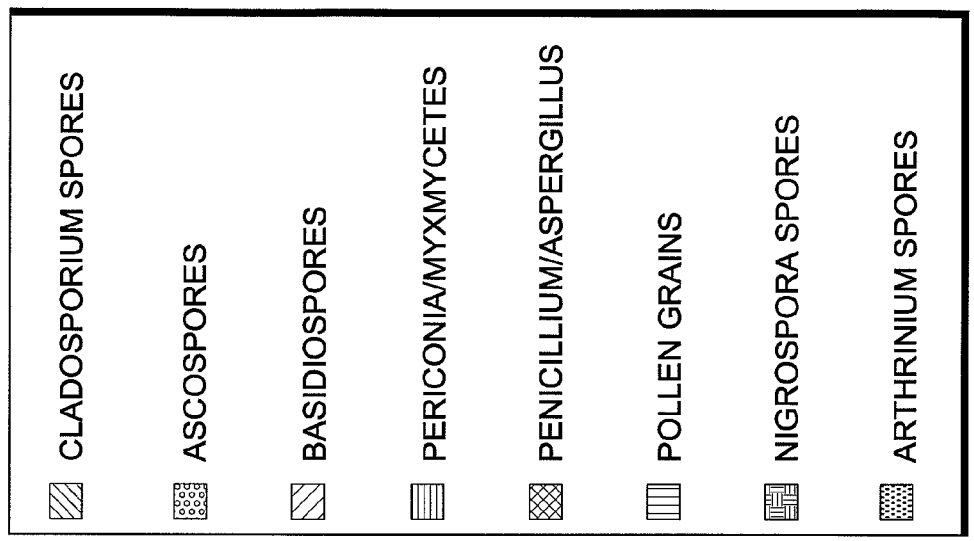
FIG. 2 provides levels (spores/m$^3$) of *cladosporium* spores, ascospores, basidiospores, *periconia*/myxomycetes, *penicillium/aspergillus*, algae, ganodera basidiospores, and *alternaria* spores in the air in a dining room of a Santa Monica, Calif. home before and after treatment, and outdoors.
Figure 2:
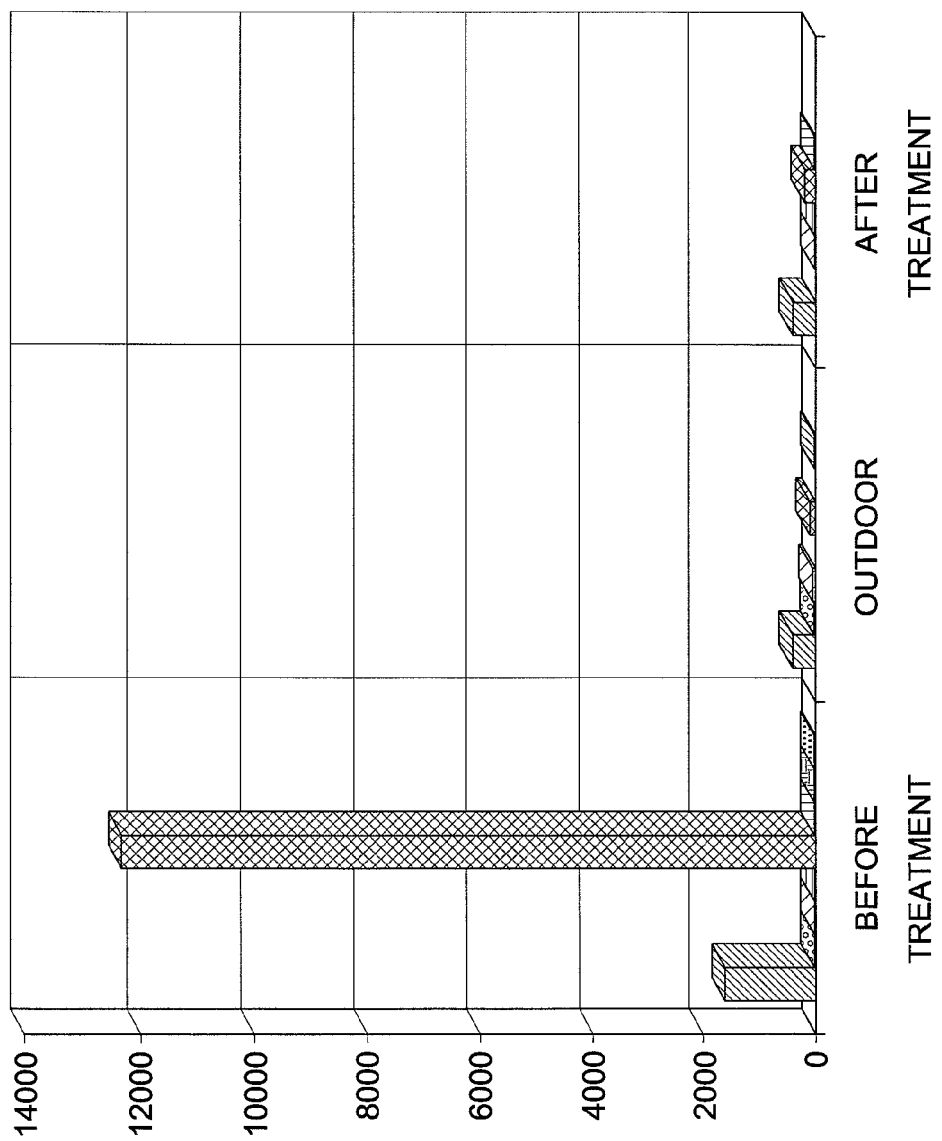
Figure 3:
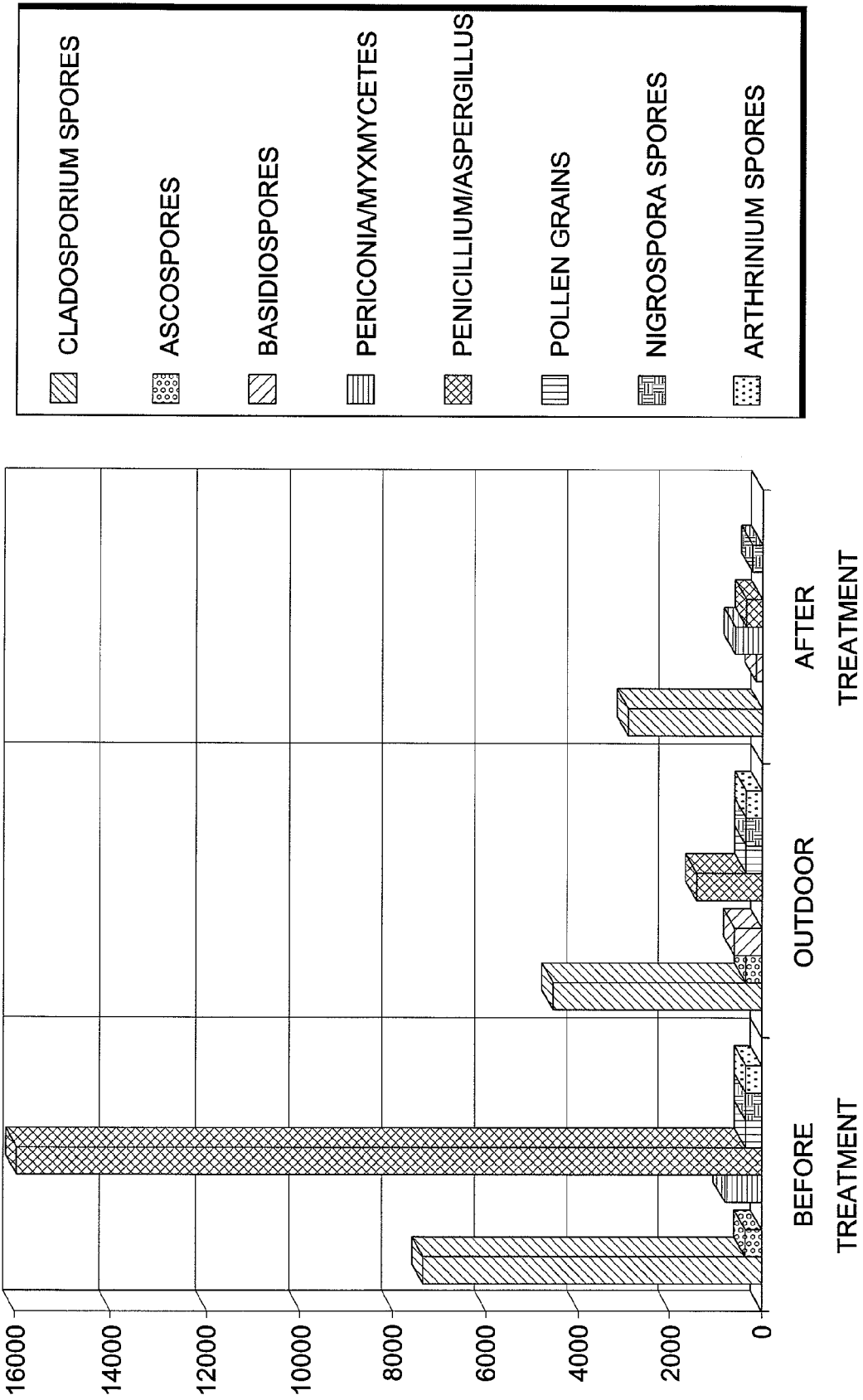
FIG. 3 provides levels (spores/m$^3$) of *cladosporium* spores, ascospores, basidiospores, *periconia*/myxomycetes, *penicillium/aspergillus*, algae, ganodera basidiospores, and *alternaria* spores in the air in a master bedroom of a Santa Monica, Calif. home before and after treatment, and outdoors.
Figure 4:
FIG. 4 provides levels (spores/m$^3$) of *cladosporium* spores, ascospores, basidiospores, *periconia*/myxomycetes, *penicillium/aspergillus*, algae, ganodera basidiospores, and *alternaria* spores in the air in a second bedroom of a Santa Monica, Calif. home before and after treatment, and outdoors.
Figure 4:
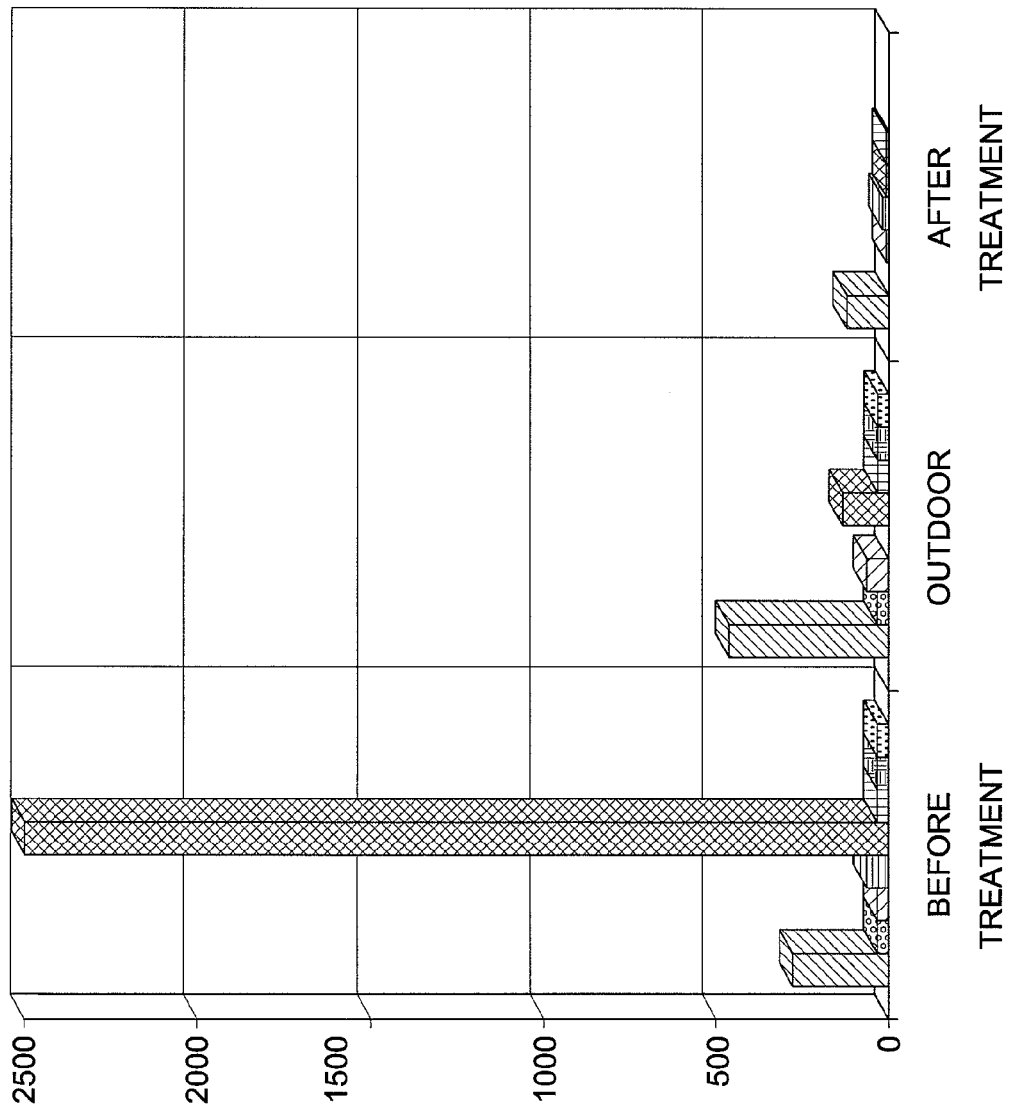

A private residence located in Santa Monica, Calif. was treated with ozone according to a preferred method. A full study of the "before treatment" and "after treatment" conditions in the house was conducted by an independent Indoor Air Quality specialist. The testing portion of the study consisted of taking air samples outside the house to determine background levels of contaminants and in 3 rooms within the house. These tests were conducted on Feb. 14, 2002 (before treatment) and then again on Feb. 21, 2002 (after treatment). The results of the study showed that, in the two bedrooms tested, all types of identified mold spores were reduced below that of the outdoor air (i.e., a 100% kill), while in the dining room the very high levels of *Penicillium/Aspergillus* (12,339 spores/m$^3$) were reduced by more than 99% while the levels all other fungi types were equal to or below that of the outdoor air (a 100% kill). The graphs provided in FIGS. 2, 3, and 4 provide a visual representation of the results obtained in the Santa Monica home's dining room, master bedroom, and second bedroom, respectively, and are typical of the results obtained using the method of the preferred embodiments.

Examples of mold levels before and after treatment according to the method of the preferred embodiments are provided in Table 1. The numbers refer to total mold count for all mold types.

TABLE 1

| Treatment | Location | Total Mold Count (spores/m$^3$) | |
|---|---|---|---|
| | | Before | After |
| 1 | Master Bath Skylight | 30,900 | 681 |
| 1 | Master Bath Above Shower | 526,000 | 0 |
| 1 | Family Room Ceiling | 641,000 | 0 |
| 2 | Above Shower | 672,000 | 0 |
| 2 | Bedroom/Closet Wall | 18 | 0 |
| 2 | entry Closet | 86,900 | 276 |
| 3 | Master Bedroom | 8,620 | 755 |
| 3 | Shower | 110 | 0 |
| 4 | n/a | 200 | 5 |
| 5 | Garage | 43,200 | 681 |

All references cited herein are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for abating a substance, the method comprising the step of:
   exposing a substance selected from the group consisting of a pathogen, an allergen, and an odor-causing agent to a gaseous atmosphere comprising water vapor, ozone, and hydrogen peroxide, wherein the atmosphere has an ozone concentration of from about 2 to about 10 parts per million, a relative humidity of from about 50% to about 90%, a hydrogen peroxide concentration that is from about 75% to about 150% by weight of the ozone concentration, and a temperature of from about 15° C. to about 27° C., wherein the substance is exposed to the atmosphere for a time period of from about 0.5 hours to about 3 hours, whereby the substance is abated.

2. The method of claim 1, wherein the pathogen is selected from the group consisting of mold, Norwalk virus, and anthrax.

3. The method of claim 1, wherein the allergen is selected from the group consisting of dust mite feces, dander, tobacco smoke, and a protein capable of inducing an allergic reaction in a human susceptible thereto.

4. The method of claim 1, wherein the odor-causing agent is selected from the group consisting of a volatile organic compound and urine.

5. A method for abating a substance in a space, the method comprising the steps of:
   sealing a space such that conditions of ozone concentration, temperature, hydrogen peroxide concentration, and relative humidity within the space can be controlled, wherein the space contains at least one substance selected from the group consisting of a pathogen, an allergen, and odor-causing agent;
   maintaining an atmospheric ozone concentration in the space of from about 2 parts per million to about 10 parts per million;
   maintaining an atmospheric hydrogen peroxide concentration in the space, wherein the atmospheric hydrogen peroxide concentration is from about 75% by weight to about 150% by weight of that of the atmospheric ozone concentration;
   maintaining a relative humidity within the space of from about 50% to about 90%; and
   maintaining a temperature within the space of from about 15° C. to about 27° C.;
   wherein the steps are conducted substantially simultaneously for a time period of from about 0.5 hours to about 3 hours, whereby the substance is abated.

6. The method of claim 5, further comprising the step of:
   ceasing providing ozone to the space; and thereafter
   exposing an interior of the space to ultraviolet light, whereby an odor associated with ozone is reduced.

7. The method of claim 5, further comprising the step of:
   ceasing providing ozone to the space; and thereafter
   exposing the space to a temperature above 27° C., whereby an odor associated with ozone is reduced.

8. The method of claim 5, further comprising the step of:
   providing ions to the space, whereby an odor associated with ozone is reduced.

9. The method of claim 5, wherein the space comprises an interior portion of a building.

10. The method of claim 5, wherein the space comprises a room of a building.

11. The method of claim 10, wherein the building comprises a dwelling.

12. The method of claim 5, wherein the space comprises an interior portion of a ship.

13. The method of claim 5, wherein the space comprises an interior portion of passenger car.

14. The method of claim 5, wherein the space comprises an interior portion a mobile home or a motor home.

15. The method of claim 5, wherein the pathogen is mold.

16. The method of claim 5, wherein the pathogen is selected from the group consisting of Norwalk virus and anthrax.

17. The method of claim 5, wherein the allergen is selected from the group consisting of dust mite feces, dander, tobacco smoke, and a protein capable of inducing an allergic reaction in a human susceptible thereto.

18. The method of claim 5, wherein the odor-causing agent is a volatile organic compound.

19. The method of claim 5, wherein the odor-causing agent is urine.

20. A method for abating a substance in an enclosed space, the method comprising the steps of:
   providing an ingress into the space, wherein the space contains at least one substance selected from the group consisting of a pathogen, an allergen, and odor-causing agent;
   providing an egress out of the space;
   providing ozone to an atmosphere within the space via the ingress, so as to an atmospheric ozone concentration, as measured at the egress, of from about 2 ppm to about 10 ppm;
   providing hydrogen peroxide to an atmosphere within the space via the ingress, so as to maintain an atmospheric hydrogen peroxide concentration, as measured at the egress, that is at least about 75% by weight of that of the atmospheric ozone concentration;
   maintaining a relative humidity within the space of at least about 70%; and
   maintaining a temperature within the space of at least about 15° C.;
   wherein the steps are conducted substantially simultaneously for a time period of at least about 0.5 hours, whereby the substance is abated.

21. The method of claim 20, wherein the space is selected from an interior of a wall in a building, an interior of a floor in a building, and an interior of a ceiling in a building.

22. The method of claim 20, wherein the ingress and the egress are situated on substantially opposite ends of the space.

23. The method of claim 20, wherein the pathogen is mold.

24. The method of claim 20, wherein the pathogen is selected from the group consisting of Norwalk virus and anthrax.

25. The method of claim 20, wherein the allergen is selected from the group consisting of dust mite feces, dander, tobacco smoke, and a protein capable of inducing an allergic reaction in a human susceptible thereto.

26. The method of claim 20, wherein the odor-causing agent is a volatile organic compound.

27. The method of claim 20, wherein the odor-causing agent is urine.

28. The method of claim 20, wherein the space comprises an interior portion of a building.

29. The method of claim 20, wherein the space comprises a room of a building.

30. The method of claim 20, wherein the building comprises a dwelling.

31. A method for abating a substance in an enclosed space, the method comprising the steps of:
  providing an ingress into the space, wherein the space contains at least one substance selected from the group consisting of a pathogen, an allergen, and odor-causing agent;
  providing an egress out of the space;
  providing ozone to an atmosphere within the space via the ingress, so as to an atmospheric ozone concentration, as measured at the egress, of at least about 2 ppm;
  providing hydrogen peroxide to an atmosphere within the space via the ingress, so as to maintain an atmospheric hydrogen peroxide concentration, as measured at the egress, that is from about 75% by weight to about 150% by weight of that of the atmospheric ozone concentration;
  maintaining a relative humidity within the space of at least about 70%; and
  maintaining a temperature within the space of at least about 15° C.;
  wherein the steps are conducted substantially simultaneously for a time period of at least about 0.5 hours, whereby the substance is abated.

32. The method of claim 31, wherein the pathogen is mold.

33. The method of claim 31, wherein the pathogen is selected from the group consisting of Norwalk virus and anthrax.

34. The method of claim 31, wherein the allergen is selected from the group consisting of dust mite feces, dander, tobacco smoke, and a protein capable of inducing an allergic reaction in a human susceptible thereto.

35. The method of claim 31, wherein the odor-causing agent is a volatile organic compound.

36. The method of claim 31, wherein the ingress and the egress are situated on substantially opposite ends of the space.

37. The method of claim 31, wherein the space is selected from an interior of a wall in a building, an interior of a floor in a building, and an interior of a ceiling in a building.

38. The method of claim 31, wherein the space comprises an interior portion of a building.

39. The method of claim 31, wherein the space comprises a room of a building.

40. The method of claim 31, wherein the building comprises a dwelling.

* * * * *